US011676197B2

(12) United States Patent
Green et al.

(10) Patent No.: US 11,676,197 B2
(45) Date of Patent: Jun. 13, 2023

(54) AUTOMATED ELECTRONIC MEDICATION DOCUMENTATION AND SPONSORED CONTENT DELIVERY SYSTEM

(71) Applicant: MarkeTouch Media, Inc., Houston, TX (US)

(72) Inventors: Lyle M. Green, Pacific Palisades, CA (US); Charles E. Russo, Houston, TX (US); Matthew K. Feltman, Isle of Palms, SC (US)

(73) Assignee: MarkeTouch Media, LLC, Houston, TX (US)

( * ) Notice: Subject to any disclaimer, the term of this patent is extended or adjusted under 35 U.S.C. 154(b) by 190 days.

(21) Appl. No.: 16/866,547

(22) Filed: May 5, 2020

(65) Prior Publication Data

US 2021/0350444 A1 Nov. 11, 2021

(51) Int. Cl.
| | |
|---|---|
| *H04L 67/306* | (2022.01) |
| *G06Q 30/0601* | (2023.01) |
| *G16H 70/40* | (2018.01) |
| *G06Q 30/0251* | (2023.01) |
| *H04L 9/40* | (2022.01) |
| *G06F 3/12* | (2006.01) |
| *H04W 4/14* | (2009.01) |

(Continued)

(52) U.S. Cl.
CPC ....... *G06Q 30/0635* (2013.01); *G06F 3/1296* (2013.01); *G06F 16/953* (2019.01); *G06Q 30/0253* (2013.01); *G16H 70/40* (2018.01); *H04L 63/102* (2013.01); *H04L 67/02* (2013.01); *H04L 67/306* (2013.01); *H04W 4/14* (2013.01)

(58) Field of Classification Search
CPC ..... H04L 67/02; H04L 67/306; H04L 63/102; G06Q 30/0635; G06Q 30/0253; G06Q 10/10; G16H 70/40; G06F 3/1296; G06F 16/953; H04W 4/14
See application file for complete search history.

(56) References Cited

U.S. PATENT DOCUMENTS

| | | | |
|---|---|---|---|
| 10,621,645 B2 * | 4/2020 | Toupin | ............... G06Q 30/0631 |
| 2014/0114470 A1 * | 4/2014 | Rashid | ................... G16H 20/13 |
| | | | 700/235 |

(Continued)

*Primary Examiner* — Jungwon Chang
(74) *Attorney, Agent, or Firm* — Kilpatrick Townsend & Stockton LLP

(57) ABSTRACT

Techniques are described for electronic content delivery. One method includes receiving information associated with the prescription order of a user account. In some cases, the information associated with the prescription order includes a medication identifier. The method may include performing a search using the medication identifier to obtain electronic medication documentation. The method may also include transmitting a sponsored content request that includes the medication identifier and receiving sponsored content information responsive to the sponsored content request. The method may further include determining that the user account has authorized communication via a user device and transmitting the electronic medication documentation and/or sponsored content information to the user device. In some examples, the method may include transmitting an indication that the electronic medication documentation and/or sponsored content information was transmitted to the user device.

19 Claims, 12 Drawing Sheets

(51) Int. Cl.
*H04L 67/02* (2022.01)
*G06F 16/953* (2019.01)

(56) References Cited

U.S. PATENT DOCUMENTS

| | | | |
|---|---|---|---|
| 2015/0206262 A1* | 7/2015 | Pinsonneault | G06Q 10/10 |
| | | | 705/2 |
| 2018/0253682 A1* | 9/2018 | Gilman | G06Q 20/28 |
| 2018/0276611 A1* | 9/2018 | Dromerhauser | G06Q 10/0833 |
| 2019/0163876 A1* | 5/2019 | Remme | G16H 40/20 |
| 2019/0378598 A1* | 12/2019 | Johnson | G16H 20/10 |
| 2020/0098462 A1* | 3/2020 | Takashima | G07F 17/0092 |
| 2020/0294642 A1* | 9/2020 | Bostic | G16H 20/10 |

* cited by examiner

AUTOMATED ELECTRONIC MEDICATION DOCUMENTATION AND SPONSORED CONTENT DELIVERY SYSTEM

FIELD OF TECHNOLOGY

The present disclosure relates generally to electronic document distribution systems, and more specifically to automated electronic medication documentation and sponsored content delivery system.

DESCRIPTION OF RELATED ART

Companies may interact with customers via calls to the customers' home and mobile phones. Some companies have extensive interaction with their customers such that contacts with the customers can be beneficial to the services provided by these companies and to the customers. For example, a customer may engage a pharmacy to supply medicaments. As a result, the pharmacy may require post-sale contacts and/or processes associated with the customer (e.g., regarding a prescription fulfillment and pick-up). To support a company's interactions with its customers, systems have been developed as a centralized, scalable mechanism related to various customer contact contexts, including, for example, sales and marketing contacts, service order contacts, technical support issues, and billing questions. A cloud platform (i.e., a computing platform for cloud computing) or hosted platform (i.e., a privately-managed computing platform utilizing cloud computing) may be employed by varies entities to store, manage, and process data using a network of remote servers to support these systems.

SUMMARY

The described features generally relate to one or more improved methods, systems, or devices that provide techniques for providing automated electronic medication documentation and sponsored content delivery. In some examples, medication-related documentation may be accessed by a system to provide the medication-related documentation to a user in electronic form. Additionally or alternatively, sponsored content may be accessed by the system to provide the sponsored content to a user in electronic form. The server may deliver the electronic medication-related documentation and/or the electronic sponsored content to a user device. In some cases, the server may utilize a publicly-available uniform resource locator (URL) to access the medication-related documentation. In some cases, the sponsored content may be a URL accessible by the user.

A method of electronic content delivery is described. The method may include receiving information associated with the prescription order of a user account. In some cases, the information associated with the prescription order may include a medication identifier. The method may also include performing a search using the medication identifier to obtain electronic medication documentation. The method may also include transmitting a sponsored content request that includes the medication identifier. The method may also include receiving sponsored content information responsive to the sponsored content request. The method may include determining that the user account has authorized communication via a user device. The method may also include transmitting at least one of the electronic medication documentation or the sponsored content information to the user device. Additionally, the method may include transmitting an indication that at least one of the electronic medication documentation or the sponsored content information was transmitted to the user device.

A method of electronic content delivery is described. The method may include receiving information associated with a prescription order of a user account. In some cases, the information associated with the prescription may include an indication that the prescription is in a ready status and information for providing contact associated with the user account. The method may include determining that the user account has not been contacted to authorize communication via a user device. Additionally, the method may include transmitting, based on the determining that the user account has not been contacted to authorize communication via a user device, an indication that electronic content was not transmitted to the user device.

A method of electronic content delivery is described. The method may include processing a prescription order associated with a user account. The method may also include determining that at least one of medication documentation or sponsored content information is to be delivered based on a medication identifier. The method may also include obtaining information associated with the prescription order of a user account. In some cases, the information associated with the prescription order may include a medication identifier. The method may also include performing a search using the medication identifier to obtain electronic medication documentation. The method may also include transmitting a sponsored content request that includes the medication identifier. The method may also include receiving sponsored content information responsive to the sponsored content request. The method may also include determining that the user account has authorized communication via a user device, transmitting at least one of the electronic medication documentation or the sponsored content information to the user device, transmitting, to the print management server, an indication that at least one of the electronic medication documentation or the sponsored content information was transmitted to the user device, receiving, by the print management server and from the pharmacy management software system, an indication that a print job corresponding to the prescription order is required, disregarding the indication that a print job corresponding to the prescription order is required based on the indication that at least one of the electronic medication documentation or the sponsored content information was transmitted to the user device, and transmitting, by the print management server, a print suppression message associated with the print job corresponding to the prescription order.

A method of electronic content delivery is described. The method may include processing a prescription order associated with a user account. The method may also include determining that at least one of medication documentation or sponsored content information is to be delivered based on a medication identifier. The method may also include obtaining information associated with the prescription order of a user account. In some cases, the information associated with the prescription may include an indication that the prescription is in a ready status and information for providing contact associated with the user account. The method may also include determining that the user account has not been contacted to authorize communication via a user device. The method may also include transmitting, based on the determining that the user account has not been contacted to authorize communication via a user device, an indication that electronic content was not transmitted to the user device. The method may also include receiving an indication that a print job corresponding to the prescription order is required. In some cases, the method may include disregarding the indication that a print job corresponding to the prescription order is required based on an indication that at least one of the electronic medication documentation or the sponsored content information was transmitted to the user device. In some cases, the method may include transmitting, based on the indication that electronic content was not transmitted to the user device, a print message associated with the print job corresponding to the prescription order.

A method of electronic content delivery is described. The method may include processing a prescription order associated with a user account. The method may also include determining that at least one of medication documentation or sponsored content information is to be delivered based on a medication identifier. The method may also include performing a search using the medication identifier to obtain electronic medication documentation. The method may also include transmitting a sponsored content request that includes the medication identifier. The method may also include receiving sponsored content information responsive to the sponsored content request. The method may also include determining that the user account has authorized communication via a user device. The method may also include transmitting at least one of the electronic medication documentation or the sponsored content information to the user device. Additionally, the method may include transmitting an indication that at least one of the electronic medication documentation or the sponsored content information was transmitted to the user device.

A method of electronic content delivery is described. The method may include receiving an indication that a print job corresponding to the prescription order is required. The method may also include receiving information associated with the prescription order of a user account. In some cases, the information associated with the prescription order may include a medication identifier. The method may also include performing a search using the medication identifier to obtain at least one of electronic medication documentation or sponsored content information. The method may also include determining that the user account has authorized communication via a user device. The method may also include transmitting at least one of the electronic medication documentation or the sponsored content information to the user device. Additionally, the method may include and transmitting a print suppression message associated with the print job corresponding to the prescription order.

Apparatus for electronic content delivery is described. An apparatus may include a processor, memory coupled with the processor, and instructions stored in the memory. The instructions may be executable by the processor to cause the apparatus to perform one or more of the operations described in the methods described herein.

Other apparatus for electronic content delivery is described. An apparatus may include means for performing one or more of the operations described in the methods described herein.

Non-transitory computer-readable medium storing code for electronic content delivery is described. Code may include instructions executable by a processor to perform one or more of the operations described in the methods described herein.

DETAILED DESCRIPTION

Figure 1:
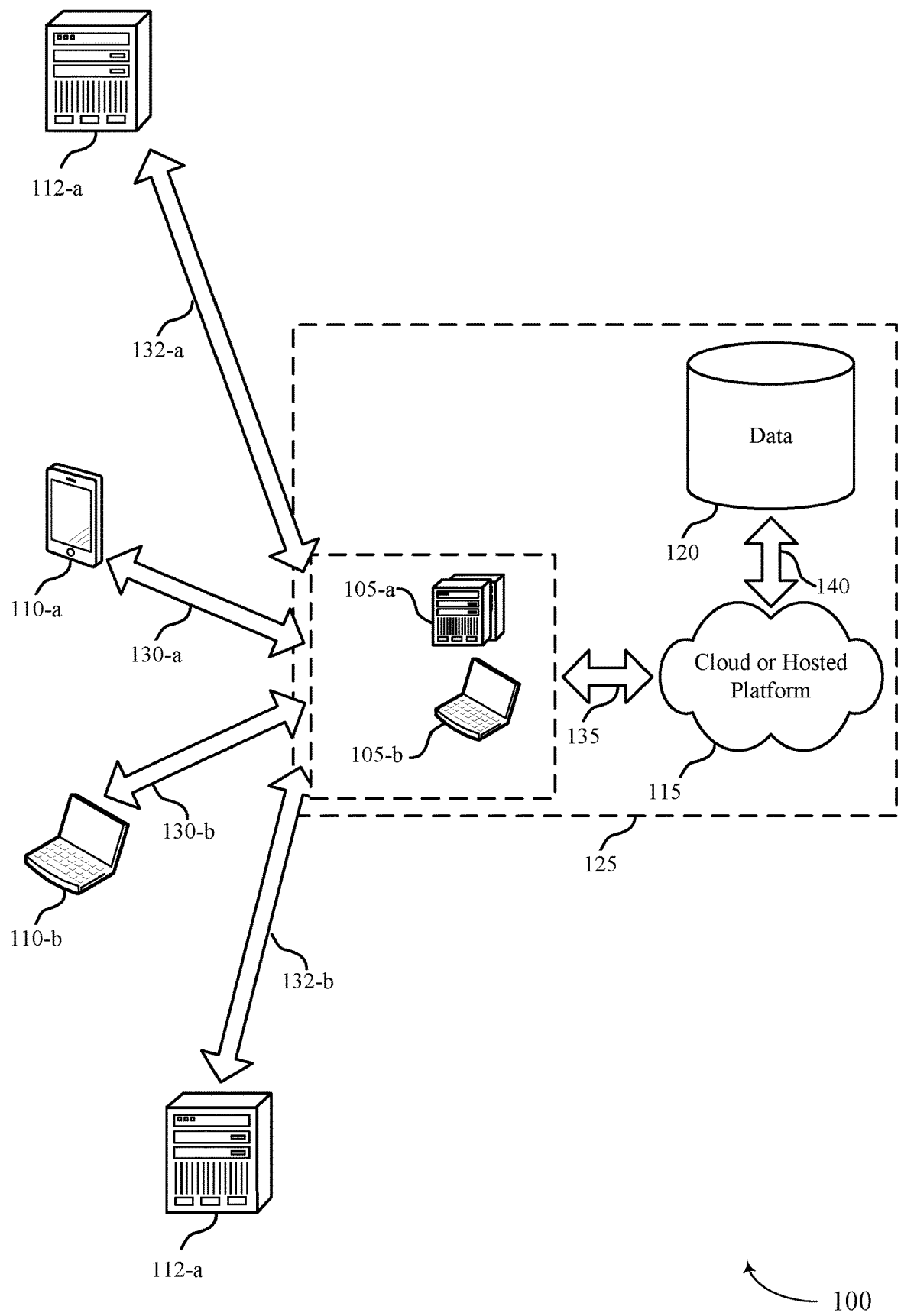
FIG. 1 illustrates an example of a system for electronic content delivery that supports automated electronic medication documentation and sponsored content delivery in accordance with aspects of the present disclosure.

In accordance with some aspects of the present disclosure, a server may receive information associated with the prescription order of a user account. In some cases, the information associated with the prescription order includes a medication identifier. For example, the medication identifier may be a drug name, a generic code number, a national drug code, or a generic product identifier. The server may perform a search using the medication identifier to obtain electronic medication documentation. The electronic medication documentation may include, but is not limited to, one or more U.S. Food and Drug Administration Medication Guides. For example, the electronic medication documentation may include Vaccine Information Statements (VISs), Risk Evaluation and Management Strategies (REMS) programs, etc. In some cases, the information associated with the prescription order may include an indication that the prescription is in a ready status. For example, a ready status may indicate that the prescription has been processed by a pharmacy and is ready for pick-up by a customer of the pharmacy that is associated with the user account. In some cases, the information associated with the prescription order may include information for providing contact associated with the user account. For example, information for providing contact may include a primary contact number or a patient identifier. In some cases, both the primary contact number and the patient identifier are included in the information for providing contact associated with the user account.

Additionally or alternatively, the server may transmit a sponsored content request that includes the medication identifier. Responsive to this sponsored content request, the server may receive sponsored content information. That is, electronic content information in addition to electronic medication documentation may be requested and acquired by the server. In some examples, the server may acquire the sponsored content information absent a request transmitted to another server. Rather, the server may cross-reference the medication identifier with a database accessible by the server to ascertain sponsored content information. In some cases, the sponsored content information may comprise a URL.

The server may determine whether the user account has authorized communication via a user device. For example, when the server has determined the user account has authorized communication via the user device, the server transmits the electronic medication documentation and/or sponsored content information to the user device. In some cases, the server may determine that the user account has not authorized communication via the user device. For example, the server may determine that the user account does not include a device authorized to receive text messages or electronic transmissions. In some cases, the server may determine not to communicate via the user device based on the server identifying that the electronic medication documentation and/or sponsored content information to be delivered is a first instance for delivery of such eligible content, for example, even if the user device has been authorized to receive text messages or electronic transmissions.

In some examples, the server may transmit an indication that the electronic medication documentation or sponsored content information was transmitted to the user device. For example, the server may transmit the indication to another server (e.g., a server associated with a print management software system or a pharmacy management software system), so that the other server and associated system is aware that electronic information was delivered to a customer of the user device. Such an indication confirming that the electronic content was delivered to the customer of the user device may enable the other server (or other servers) to forego certain steps or operations it would normally perform (e.g., forego printing medication documentation when the customer arrives at the pharmacy to pick-up the prescription).

In some examples, the medication identifier may comprise a national drug code, generic code number, or a generic product identifier. In some cases, the medication identifier may be a name of the mediation. For example, portions of the national drug code may indicate information that can be used to ascertain whether sponsored content is available for the prescription order. A first section may identify the drug product itself. A second section may identify a manufacturer of the drug product. A third section pack size into which the manufacturer placed the drug product. Additionally or alternatively, a generic code number or a generic product identifier may be used to indicate information that can be used to ascertain whether sponsored content is available for the prescription order. A generic code number or a generic product identifier may identify a medication type without information about the manufacturer. A generic code number or a generic product identifier may be used to link sponsored content that relates to the medication irrespective of the manufacturer.

Sponsored content may be related to the medication included the prescription order. For example, when taking a prescription statin (e.g., Lipitor) for lowering cholesterol levels, it may be recommended to take an over the counter supplements like CoQ10. Sponsored content may include a coupon for a CoQ10 seller where the sponsored content is linked to a prescription including a statin identifiable by a portion of the medication identifier. In another non-limiting example, if the medication included the prescription order includes inhaled corticosteroids for an asthma condition, sponsored content may include instructions for using a smart metered-dose inhaler (e.g., a URL to an instructional video or documentation).

In other examples, sponsored content may be unrelated to the medication included the prescription order. For example, sponsored content may be temporally and/or facility related. If a date of the prescription order corresponds to a particular facility during a specific time of the year (e.g., Flu season), sponsored content may include a notice and/or discount for Flu shot available to be administered at the pharmacy.

Aspects of the disclosure are initially described in the context of an environment supporting a database. A server may access the database to provide electronic content delivery. Aspects of the disclosure are further illustrated by and described with reference to apparatus diagrams, system diagrams, and flowcharts that relate to automated electronic medication documentation and sponsored content delivery system.

FIG. 1 illustrates an example of a system 100 for cloud computing that supports automated electronic medication documentation and sponsored content delivery in accordance with various aspects of the present disclosure. The system 100 includes client 105 (e.g., a cloud client or hosted client), user device contacts 110, remote system contacts 112, cloud platform 115, and data access 120. Cloud platform 115 may be an example of a public or private cloud network. A client 105 may access cloud platform 115 over network connection 135. The network may implement transfer control protocol and internet protocol (TCP/IP), such as the Internet, or may implement other network protocols. A client 105 may be an example of a user device, such as a server (e.g., client 105-a) or a laptop (e.g., client 105-b). In other examples, a client 105 may be a desktop computer, a tablet, or another computing device or system capable of generating, analyzing, transmitting, or receiving communications. In some examples, a client 105 may be operated by a user entity that is part of a business or other organization type (e.g., an entity responsible for providing consumer contact).

A client 105 may interact with multiple user device contacts 110. The interactions 130 may include communications, opportunities, purchases, sales, or any other interaction between a client 105 and a user device contact 110. Data may be associated with the interactions 130. A client 105 may access cloud or hosted platform 115 to store, manage, and process the data associated with the interactions 130. In some cases, the client 105 may have an associated security or permission level. A client 105 may have access to certain applications, data, and database information within cloud or hosted platform 115 based on the associated security or permission level, and may not have access to others.

Client 105 may interact with user device contacts 110 via text messaging, email, voice call, or any other appropriate form of interaction (e.g., interactions 130-a, or 130-b). In some examples, the interaction 130 may be a business-to-consumer (B2C) interaction. A user device contact 110 may also be referred to as or associated with a consumer, a customer, or some other suitable terminology. In some cases, the user device contact 110 may be an example of a user device, such as a mobile device (e.g., user device contact 110-a) or a laptop (e.g., user device contact 110-b). In other cases, the user device contact 110 may be another computing device that a consumer may own capable of electronic communication. In some cases, the user device contact 110 may be operable by a consumer or user authorized to access a user account.

Client 105 may also interact with remote system contacts 112 via application programming interface (API), web communication, or any other appropriate form of interaction or computing interface (e.g., interactions 132-a, or 132-b). In some examples, the interaction 130 may be a business-to-business (B2B) interaction. A remote system contact 112 may also be referred to as a third-party system, third-party entity, or some other suitable terminology. In some cases, the remote system contacts 112 may be an example of a server at a first location (e.g., remote system contact 112-a) or a server at a second location (e.g., remote system contact 112-b). In other cases, the remote system contact 112 may be another computing system. In some cases, the remote system contact 112 may be operated by one or more users or an entity different from users or an entity associated with client 105. In other cases, the remote system contact 112 may be operated by the same users or entity as the those associated with client 105.

Cloud or hosted platform 115 may provide data access or database service for the client 105. In some cases, cloud or hosted platform 115 may be an example of a single-tenant or multi-tenant database system. However, other types of systems may be implemented, including—but not limited to—client-server systems, mobile device systems, and mobile network systems. In some cases, cloud or hosted platform 115 may support customer relationship management (CRM) solutions. In some examples, the CRM solutions may include support for consumer contact, order and service fulfillment, marketing, etc. Cloud or hosted platform 115 may receive data associated with contact interactions 130 from the client 105 over network connection 135. Cloud or hosted platform 115 may receive data associated with contact interactions 132 from the client 105 over network connection 135. In some cases, cloud or hosted platform 115 may receive data directly from an interaction 130 between a user device contact 110 and the client 105. In some cases, the user device contact 110 may run an application that includes communication with client 105 and/or cloud or hosted platform 115. Cloud or hosted platform 115 may be implemented using remote servers. In some cases, the remote servers may be located at one or more data centers 120.

Data center 120 may include multiple servers. The multiple servers may be used for data storage, management, and processing. Data center 120 may receive data from cloud or hosted platform 115 via connection 140, or directly from the client 105, or an interaction 130 between a user device contact 110 and the client 105, or an interaction 132 between a remote system contact 112 and the client 105. Data center 120 may utilize multiple redundancies for security purposes. In some cases, the data stored at data center 120 may be backed up by copies of the data at a different data center (not pictured).

Subsystem 125 may include clients 105, cloud or hosted platform 115, and data center 120. In some cases, data processing may occur at any of the components of subsystem 125, or at a combination of these components. In some cases, servers may perform the data processing. The servers may be a client 105 or located at data center 120.

In accordance with some implementations, client 105 (e.g., one or more consumer preference and maintenance interface servers) may receive, from a first remote system contact 112 (e.g., a pharmacy management software system), information associated with the prescription order of a user account, where the information associated with the prescription order includes a medication identifier. Client 105 may perform a search using the medication identifier to obtain electronic medication documentation. Client 105 may transmit, to a second remote system contact 112 (e.g., a print management software system) a sponsored content request that includes the medication identifier. Client 105 may receive, from the second remote system contact 112, sponsored content information responsive to the sponsored content request. Client 105 may determine that the user account has authorized communication via a user device (e.g., user device contact 110). Client 105 may transmit at least one of the electronic medication documentation or the sponsored content information to the user device. Client 105 may transmit, to the second remote system contact 112, an indication that at least one of the electronic medication documentation or the sponsored content information was transmitted to the user device.

In accordance with some implementations, client 105 (e.g., one or more consumer preference and maintenance interface servers) may receive, from a first remote system contact 112 (e.g., a pharmacy management software system), information associated with the prescription order of a user account, where the information associated with the prescription includes an indication that the prescription is in a ready status and information for providing contact associated with the user account. Client 105 may determine that the user account has not been contacted to authorize communication via a user device (e.g., user device contact 110). Client 105 may transmit, to a second remote system contact 112 (e.g., a print management software system) and based on the determining that the user account has not been contacted to authorize communication via a user device, an indication that electronic content was not transmitted to the user device.

In accordance with some implementations, client 105 (e.g., one or more servers associated with a pharmacy management software system) may process a prescription order associated with a user account. Client 105 may determine that at least one of medication documentation or sponsored content information is to be delivered based on a medication identifier. Client 105 may obtain, from the pharmacy management software system, information associated with the prescription order of a user account, where the information associated with the prescription order includes a medication identifier, perform a search using the medication identifier to obtain electronic medication documentation, transmit, to a print management server, a sponsored content request that includes the medication identifier, receive, from the print management server, sponsored content information responsive to the sponsored content request, determine that the user account has authorized communication via a user device, transmit at least one of the electronic medication documentation or the sponsored content information to the user device, transmit, to the print management server, an indication that at least one of the electronic medication documentation or the sponsored content information was transmitted to the user device, receive, by the print management server and from the pharmacy management software system, an indication that a print job corresponding to the prescription order is required, disregard the indication that a print job corresponding to the prescription order is required based on the indication that at least one of the electronic medication documentation or the sponsored content information was transmitted to the user device, and transmit, by the print management server, a print suppression message associated with the print job corresponding to the prescription order.

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
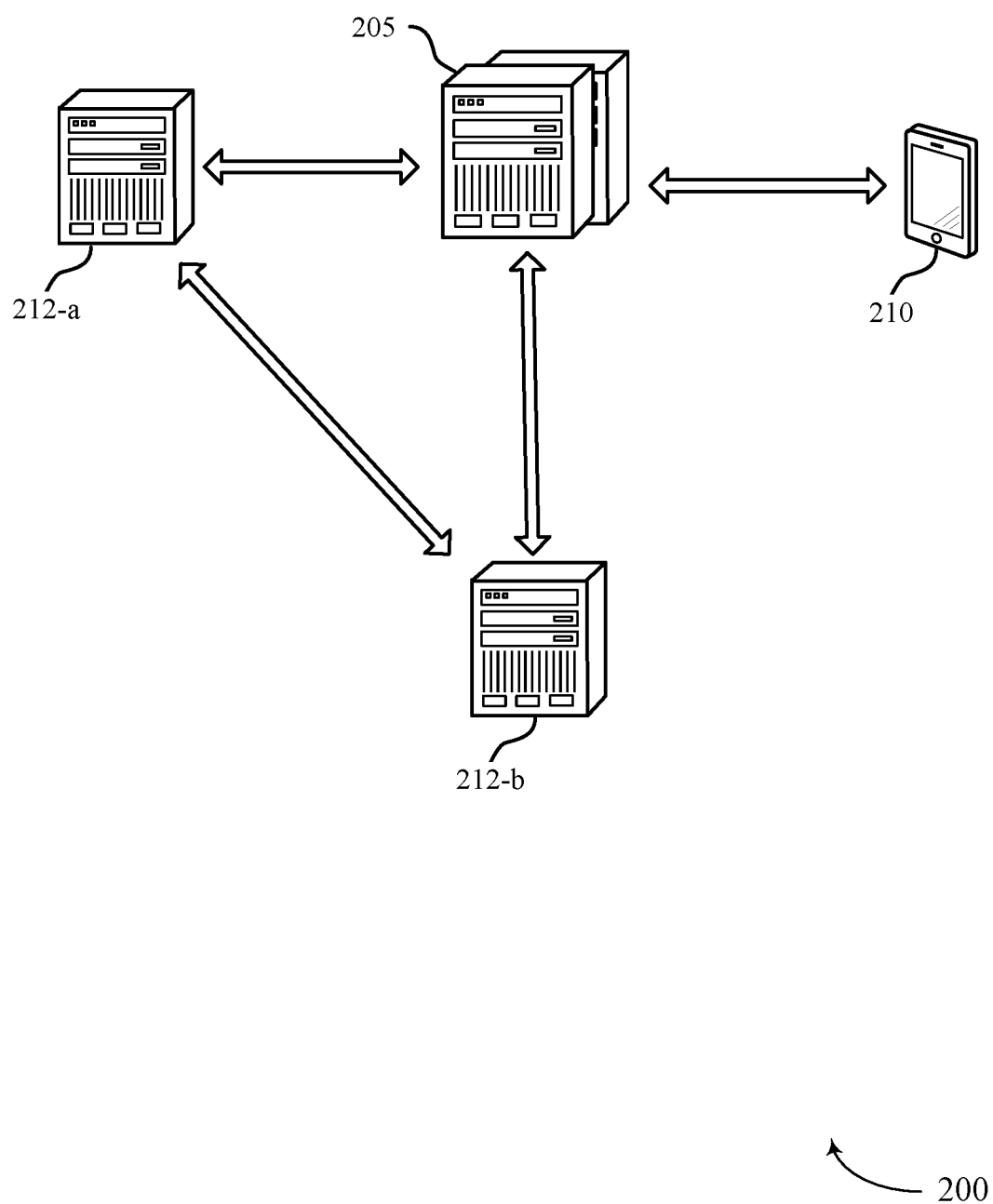
FIG. 2 shows a block diagram of an apparatus that supports automated electronic medication documentation and sponsored content delivery in accordance with aspects of the present disclosure.

FIG. 2 shows a block diagram 200 of a client 205 (e.g., one or more consumer preference and maintenance interface servers) that supports automated electronic medication documentation and sponsored content delivery system in accordance with aspects of the present disclosure. A pharmacy management software system 212-a may process a prescription order associated with a user account. The pharmacy management software system 212-a may determine that at least one of medication documentation or sponsored content information is to be delivered based on a medication identifier. For example, the pharmacy management software system 212-a may determine a prescription ready status and medication data is to be sent to client 205 for patient notification. That is, pharmacy management software system 212-a may obtain information associated with the prescription order of a user account. In some case, the information associated with the prescription order may include a medication identifier.

Based on receiving information from the pharmacy management software system 212-a, client 205 may perform a search using the medication identifier to obtain electronic medication documentation. In some cases, client 205 may transmit a sponsored content request to a print management server 212-b. The sponsored content request may include the medication identifier. client 205 may receive sponsored content information from the print management server 212-b responsive to the sponsored content request. In some examples, sponsored content may be obtained based on information contained in the electronic medication documentation. For example, client 205 may perform a search using the medication identifier to obtain the electronic medication documentation. Client 205 may identify a sponsored content relationship based at least in part on information in the electronic medication documentation. Client 205 may obtain sponsored content information based on the sponsored content relationship (i.e., rather than or in addition to the medication identifier). That is, obtaining sponsored content information may include transmitting a sponsored content request associated with the sponsored content relationship and receiving sponsored content information responsive to the sponsored content request.

Client 205 may determine that the user account has authorized communication via a user device contact 210. For example, client 205 may determine that the user account has opted in to receiving short messaging service (SMS) text messaging. Client 205 may transmit at least one of the electronic medication documentation or the sponsored content information to the user device contact 210. Client 205 may transmit an indication to print management server 212-b that at least one of the electronic medication documentation or the sponsored content information was transmitted to the user device contact 210.

In some examples, the print management server 212-b may receive an indication from the pharmacy management software system 212-a that a print job corresponding to the prescription order is required. In some cases, the print management server 212-b may disregard the indication that the print job corresponding to the prescription order is required based on the indication from the client 205 that at least one of the electronic medication documentation or the sponsored content information was transmitted to the user device contact 210. The print management server 212-b may transmit a print suppression message associated with the print job corresponding to the prescription order to pharmacy management software system 212-a. For example, the print suppression message may indicate that the print job was not performed by the print management server 212-b.

Figure 3:
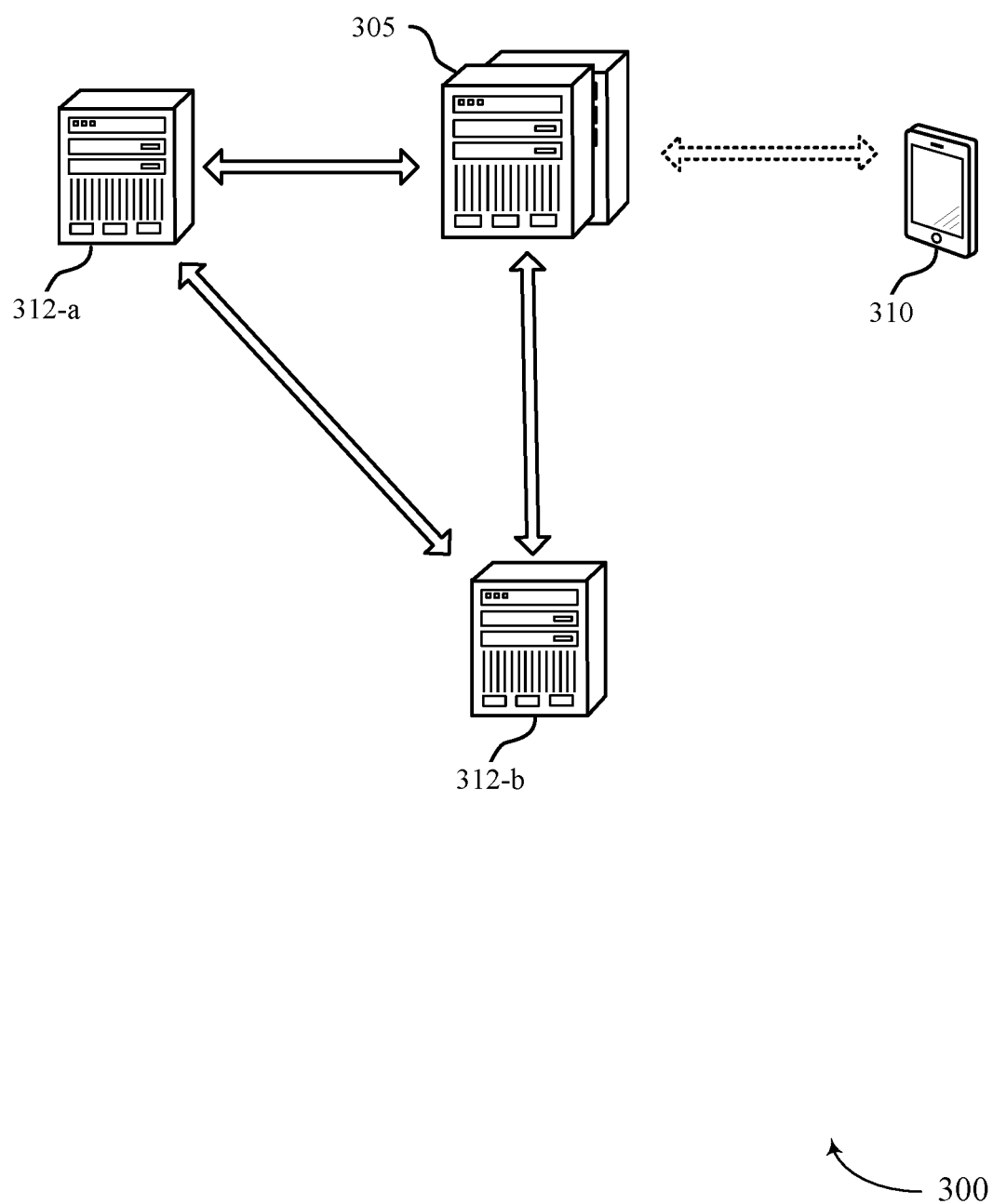
FIG. 3 shows a block diagram of an electronic content delivery manager that supports automated electronic medication documentation and sponsored content delivery in accordance with aspects of the present disclosure.

FIG. 3 shows a block diagram 300 of a server apparatus 305 (e.g., one or more consumer preference and maintenance interface servers) that supports automated electronic medication documentation and sponsored content delivery system in accordance with aspects of the present disclosure. A pharmacy management software system 312-a may process a prescription order associated with a user account. The pharmacy management software system 312-a may determine that at least one of medication documentation or sponsored content information is to be delivered based on a medication identifier. The pharmacy management software system 312-a may obtain information associated with the prescription order of a user account. In some cases, the information associated with the prescription may include an indication that the prescription is in a ready status and information for providing contact associated with the user account. In some cases, the information for providing contact associated with the user account may include a primary contact number or a patient identifier.

Based on receiving information from the pharmacy management software system 312-a, client 305 may determine that the user account has not been contacted to authorize communication via a user device contact 310. In some cases, the client 305 may determine that the user account has not been contacted to authorize communication via a user device by determining that the information associated with the prescription order of the user account is a first instance for receiving information for providing contact associated with the user account. Client 305 may transmit based on the determining that the user account has not been contacted to authorize communication via a user device (e.g., user device contact 310) an indication to a print management server 312-b that electronic content was not transmitted to a user device.

The print management server 312-b may receive an indication from the pharmacy management software system 312-a that a print job corresponding to the prescription order is required. Based on the indication from the client 305, print management server 312-b may process that print job. The print management server 312-b may transmit a print message associated with the print job corresponding to the prescription order to pharmacy management software system 312-a. For example, the print message may indicate that the print job was performed by the print management server 312-b.

In some cases, the client 305 may identify a text-capable contact number associated with the information for providing contact associated with the user account. The client 305 may notify a user of the user account via the text-capable contact number to authorize communication via a user device based on the determining that the user account has not been contacted to authorize communication via a user device. In some cases, the client 305 may identify a contact number associated with the information for providing contact associated with the user account. the client 305 may place an outbound call to the contact number based on receiving the receiving information associated with the prescription order of the user account. the client 305 may provide a message and a prompt to indicate whether to provide printed medication documentation at a location (e.g., at the pharmacy) or electronic medication documentation via a user device (e.g., via user device contact 310). If the user associated with the user account elects to electronic medication documentation via a user device, the client 305 may determine that the user account has been contacted to authorize communication via a user device for a second and subsequent prescription order associated with the user account.

Figure 4:
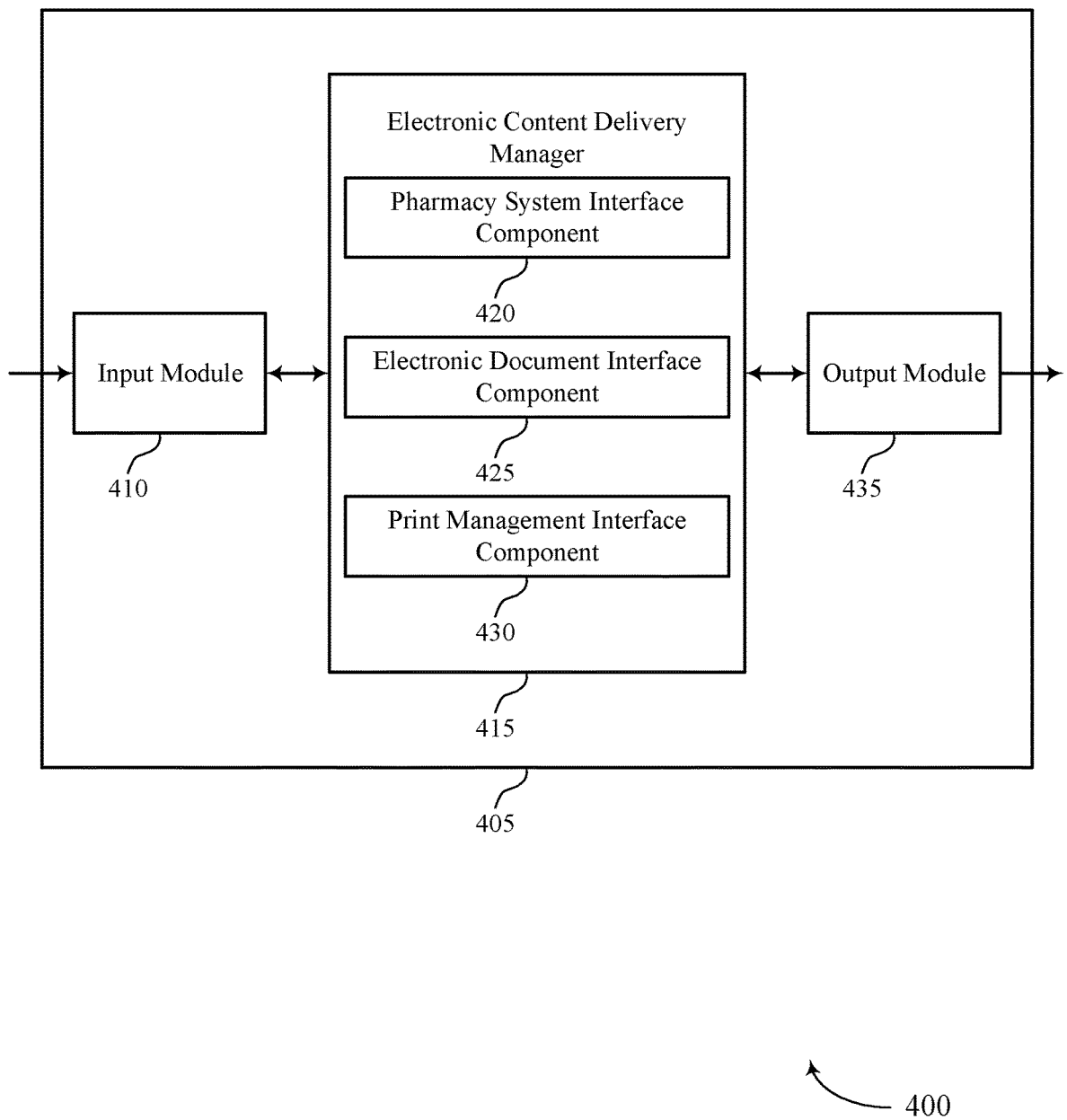
FIG. 4 shows a diagram of a system including a device that supports automated electronic medication documentation and sponsored content delivery in accordance with aspects of the present disclosure.

FIG. 4 shows a block diagram 400 of an apparatus 405 that supports automated electronic medication documentation and sponsored content delivery system in accordance with aspects of the present disclosure. The apparatus 405 may include an input module 410, an electronic content delivery manager 415, and an output module 435. The apparatus 405 may also include a processor. Each of these components may be in communication with one another (e.g., via one or more buses). In some cases, the apparatus 405 may be an example of a user terminal, a server (e.g., a database server), or a system containing multiple computing devices.

The input module 410 may manage input signals for the apparatus 405. For example, the input module 410 may identify input signals based on an interaction with a modem, a keyboard, a mouse, a touchscreen, or a similar device. These input signals may be associated with user input or processing at other components or devices. In some cases, the input module 610 may utilize an operating system such as iOS®, ANDROID®, MS-DOS®, MS-WINDOWS®, OS/2®, UNIX®, LINUX®, or another known operating system to handle input signals. The input module 410 may send aspects of these input signals to other components of the apparatus 405 for processing. For example, the input module 410 may transmit input signals to the electronic content delivery manager 415 to support automated electronic medication documentation and sponsored content delivery system. In some cases, the input module 410 may be a component of an input/output (I/O) controller 415 as described with reference to FIG. 4.

The electronic content delivery manager 415 may include a pharmacy system interface component 420, an electronic document interface component 425, and a print management interface component 430. The electronic content delivery manager 415 may be an example of aspects of the electronic content delivery manager 305 or 410 described with reference to FIGS. 3 and 4.

The electronic content delivery manager 415 and/or at least some of its various sub-components may be implemented in hardware, software executed by a processor, firmware, or any combination thereof. If implemented in software executed by a processor, the functions of the electronic content delivery manager 415 and/or at least some of its various sub-components may be executed by a general-purpose processor, a digital signal processor (DSP), an application-specific integrated circuit (ASIC), a field-programmable gate array (FPGA) or other programmable logic device, discrete gate or transistor logic, discrete hardware components, or any combination thereof designed to perform the functions described in the present disclosure. The electronic content delivery manager 415 and/or at least some of its various sub-components may be physically located at various positions, including being distributed such that portions of functions are implemented at different physical locations by one or more physical devices. In some examples, the electronic content delivery manager 415 and/or at least some of its various sub-components may be a separate and distinct component in accordance with various aspects of the present disclosure. In other examples, the electronic content delivery manager 415 and/or at least some of its various sub-components may be combined with one or more other hardware components, including but not limited to an I/O component, a transceiver, a network server, another computing device, one or more other components described in the present disclosure, or a combination thereof in accordance with various aspects of the present disclosure.

The pharmacy system interface component 420 may receive information associated with the prescription order of a user account, where the information associated with the prescription order includes a medication identifier.

The electronic document interface component 425 may perform a search using the medication identifier to obtain electronic medication documentation, transmit a sponsored content request that includes the medication identifier, receive sponsored content information responsive to the sponsored content request, determine that the user account has authorized communication via a user device, and transmit at least one of the electronic medication documentation or the sponsored content information to the user device.

The print management interface component 430 may transmit an indication that at least one of the electronic medication documentation or the sponsored content information was transmitted to the user device.

The output module 435 may manage output signals for the apparatus 405. For example, the output module 435 may receive signals from other components of the apparatus 405, such as the electronic content delivery manager 415, and may transmit these signals to other components or devices. In some specific examples, the output module 435 may transmit output signals for display in a user interface, for storage in a database or data store, for further processing at a server or server cluster, or for any other processes at any number of devices or systems. In some cases, the output module 435 may be a component of an I/O controller 415 as described with reference to FIG. 4.

Figure 5:
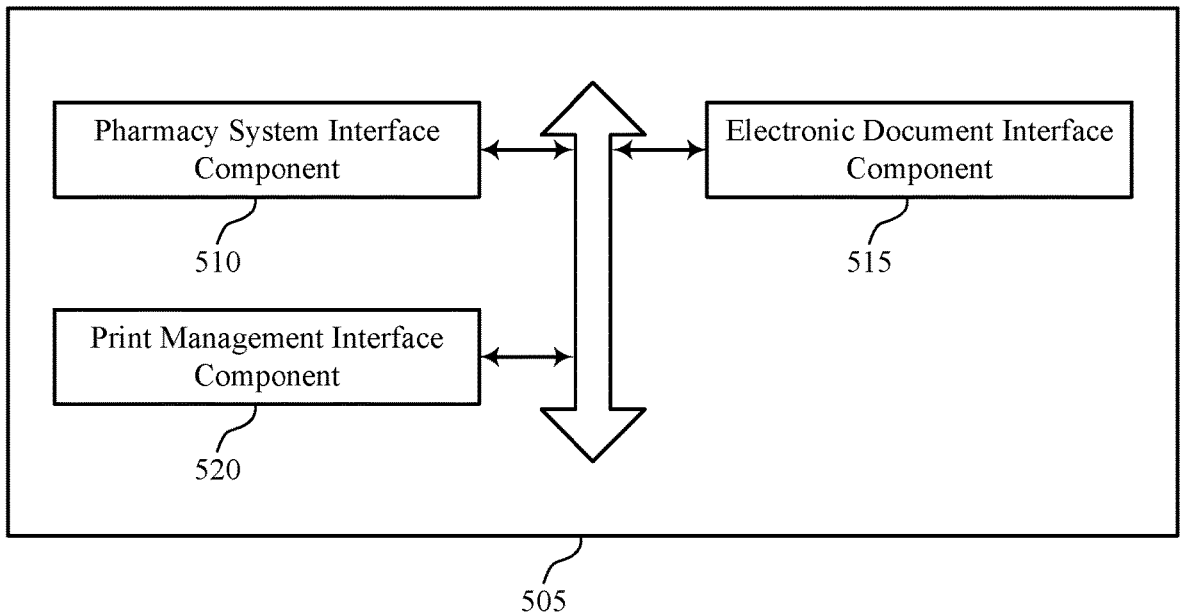
FIGS. 5 through 12 show flowcharts illustrating methods that support automated electronic medication documentation and sponsored content delivery in accordance with aspects of the present disclosure.

FIG. 5 shows a block diagram 500 of an electronic content delivery manager 505 that supports automated electronic medication documentation and sponsored content delivery system in accordance with aspects of the present disclosure. The electronic content delivery manager 505 may be an example of aspects of an electronic content delivery manager 415 or an electronic content delivery manager 410 described herein. The electronic content delivery manager 505 may include a pharmacy system interface component 510, an electronic document interface component 515, and a print management interface component 520. Each of these modules may communicate, directly or indirectly, with one another (e.g., via one or more buses).

The pharmacy system interface component 510 may receive information associated with the prescription order of a user account, where the information associated with the prescription order includes a medication identifier.

The electronic document interface component 515 may perform a search using the medication identifier to obtain electronic medication documentation. In some examples, the electronic document interface component 515 may transmit a sponsored content request that includes the medication identifier. In some examples, the electronic document interface component 515 may receive sponsored content information responsive to the sponsored content request. In some examples, the electronic document interface component 515 may determine that the user account has authorized communication via a user device. In some examples, the electronic document interface component 515 may transmit at least one of the electronic medication documentation or the sponsored content information to the user device.

The print management interface component 520 may transmit an indication that at least one of the electronic medication documentation or the sponsored content information was transmitted to the user device.

Figure 6:
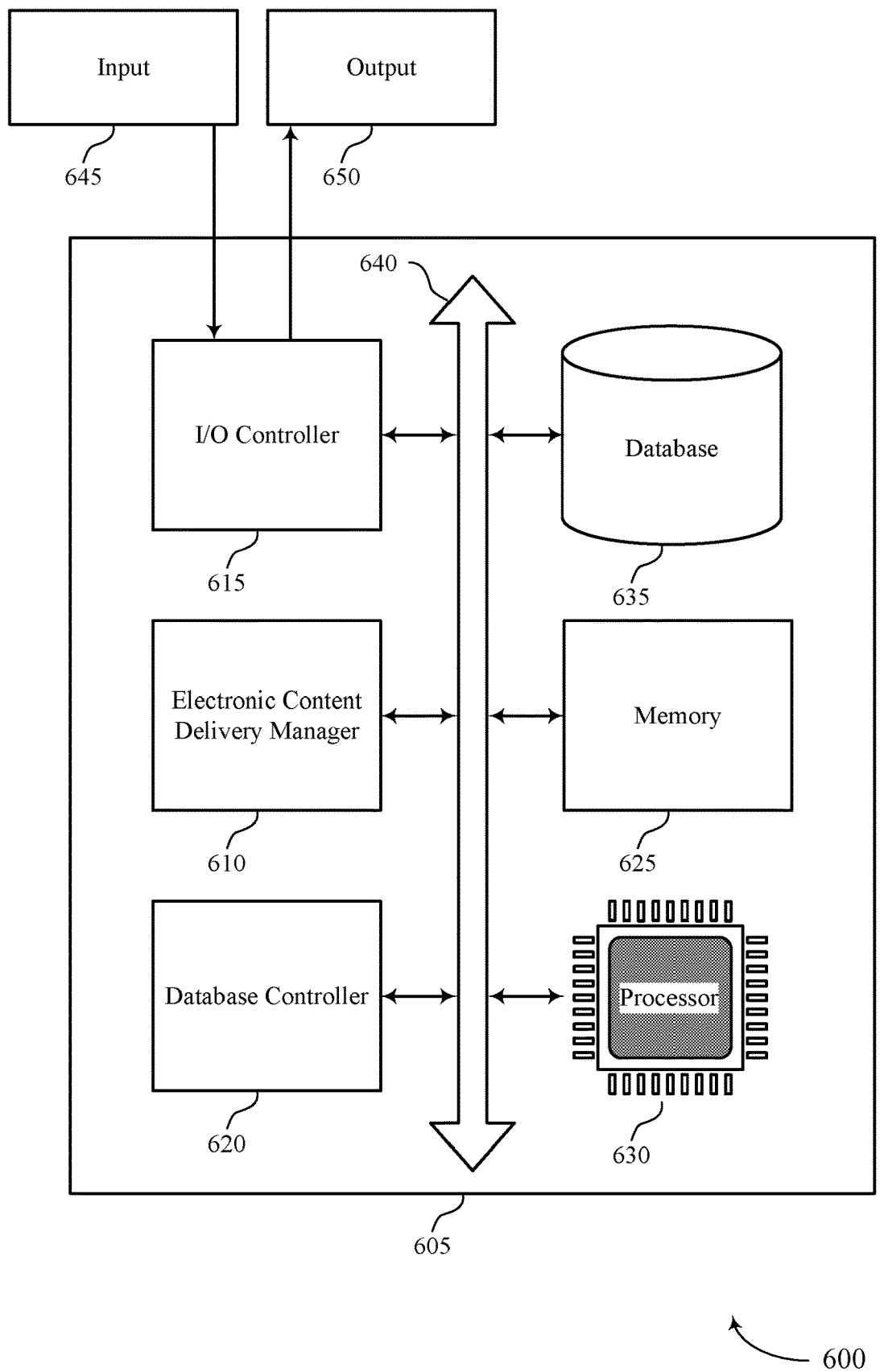

FIG. 6 shows a diagram of a system 600 including a device 605 that supports automated electronic medication documentation and sponsored content delivery system in accordance with aspects of the present disclosure. The device 605 may be an example of or include the components of a server or an apparatus 405 as described herein. The device 605 may include components for bi-directional data communications including components for transmitting and receiving communications, including an electronic content delivery manager 610, an I/O controller 615, a database controller 620, memory 625, a processor 630, and a database 635. These components may be in electronic communication via one or more buses (e.g., bus 640).

The electronic content delivery manager 610 may be an example of an electronic content delivery manager 415 or 505 as described herein. For example, the electronic content delivery manager 610 may perform any of the methods or processes described above with reference to FIGS. 4 and 5. In some cases, the electronic content delivery manager 610 may be implemented in hardware, software executed by a processor, firmware, or any combination thereof.

The I/O controller 615 may manage input signals 645 and output signals 650 for the device 605. The I/O controller 615 may also manage peripherals not integrated into the device 605. In some cases, the I/O controller 615 may represent a physical connection or port to an external peripheral. In some cases, the I/O controller 615 may utilize an operating system such as iOS®, ANDROID®, MS-DOS®, MS-WINDOWS®, OS/2®, UNIX®, LINUX®, or another known operating system. In other cases, the I/O controller 615 may represent or interact with a modem, a keyboard, a mouse, a touchscreen, or a similar device. In some cases, the I/O controller 615 may be implemented as part of a processor. In some cases, a user may interact with the device 605 via the I/O controller 615 or via hardware components controlled by the I/O controller 615.

The database controller 620 may manage data storage and processing in a database 635. In some cases, a user may interact with the database controller 620. In other cases, the database controller 620 may operate automatically without user interaction. The database 635 may be an example of a single database, a distributed database, multiple distributed databases, a data store, a data lake, or an emergency backup database.

Memory 625 may include random-access memory (RAM) and read-only memory (ROM). The memory 625 may store computer-readable, computer-executable software including instructions that, when executed, cause the processor to perform various functions described herein. In some cases, the memory 625 may contain, among other things, a basic input/output system (BIOS) which may control basic hardware or software operation such as the interaction with peripheral components or devices.

The processor 630 may include an intelligent hardware device, (e.g., a general-purpose processor, a DSP, a central processing unit (CPU), a microcontroller, an ASIC, an FPGA, a programmable logic device, a discrete gate or transistor logic component, a discrete hardware component, or any combination thereof). In some cases, the processor 630 may be configured to operate a memory array using a memory controller. In other cases, a memory controller may be integrated into the processor 630. The processor 630 may be configured to execute computer-readable instructions stored in a memory 625 to perform various functions (e.g., functions or tasks supporting automated electronic medication documentation and sponsored content delivery system).

Figure 7:
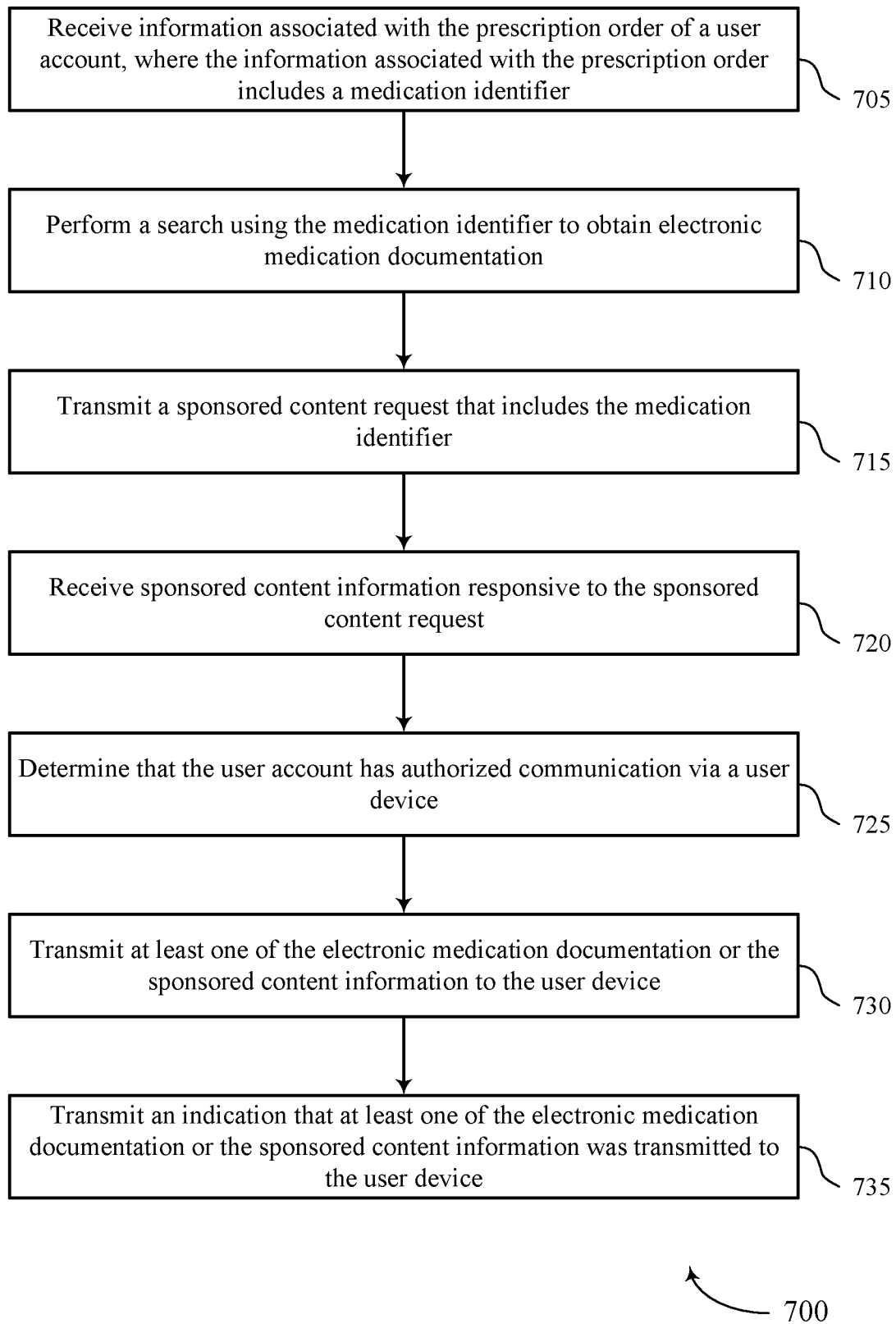

FIG. 7 shows a flowchart illustrating a method 700 that supports automated electronic medication documentation and sponsored content delivery system in accordance with aspects of the present disclosure. The operations of method 700 may be implemented by a server or its components as described herein. For example, the operations of method 700 may be performed by an electronic content delivery manager as described with reference to FIGS. 4 through 6. In some examples, a server may execute a set of instructions to control the functional elements of the server to perform the functions described below. Additionally or alternatively, a server may perform aspects of the functions described below using special-purpose hardware.

At 705, the server may receive information associated with the prescription order of a user account, where the information associated with the prescription order includes a medication identifier. The operations of 705 may be performed according to the methods described herein. In some examples, aspects of the operations of 705 may be performed by a pharmacy system interface component as described with reference to FIGS. 4 through 6.

At 710, the server may perform a search using the medication identifier to obtain electronic medication documentation. The operations of 710 may be performed according to the methods described herein. In some examples, aspects of the operations of 710 may be performed by an electronic document interface component as described with reference to FIGS. 4 through 6.

At 715, the server may transmit a sponsored content request that includes the medication identifier. The operations of 715 may be performed according to the methods described herein. In some examples, aspects of the operations of 715 may be performed by an electronic document interface component as described with reference to FIGS. 4 through 6.

At 720, the server may receive sponsored content information responsive to the sponsored content request. The operations of 720 may be performed according to the methods described herein. In some examples, aspects of the operations of 720 may be performed by an electronic document interface component as described with reference to FIGS. 4 through 6.

At 725, the server may determine that the user account has authorized communication via a user device. The operations of 725 may be performed according to the methods described herein. In some examples, aspects of the operations of 725 may be performed by an electronic document interface component as described with reference to FIGS. 4 through 6.

At 730, the server may transmit at least one of the electronic medication documentation or the sponsored content information to the user device. The operations of 730 may be performed according to the methods described herein. In some examples, aspects of the operations of 730 may be performed by an electronic document interface component as described with reference to FIGS. 4 through 6.

At 735, the server may transmit an indication that at least one of the electronic medication documentation or the sponsored content information was transmitted to the user device. The operations of 735 may be performed according to the methods described herein. In some examples, aspects of the operations of 735 may be performed by a print management interface component as described with reference to FIGS. 4 through 6.

Figure 8:
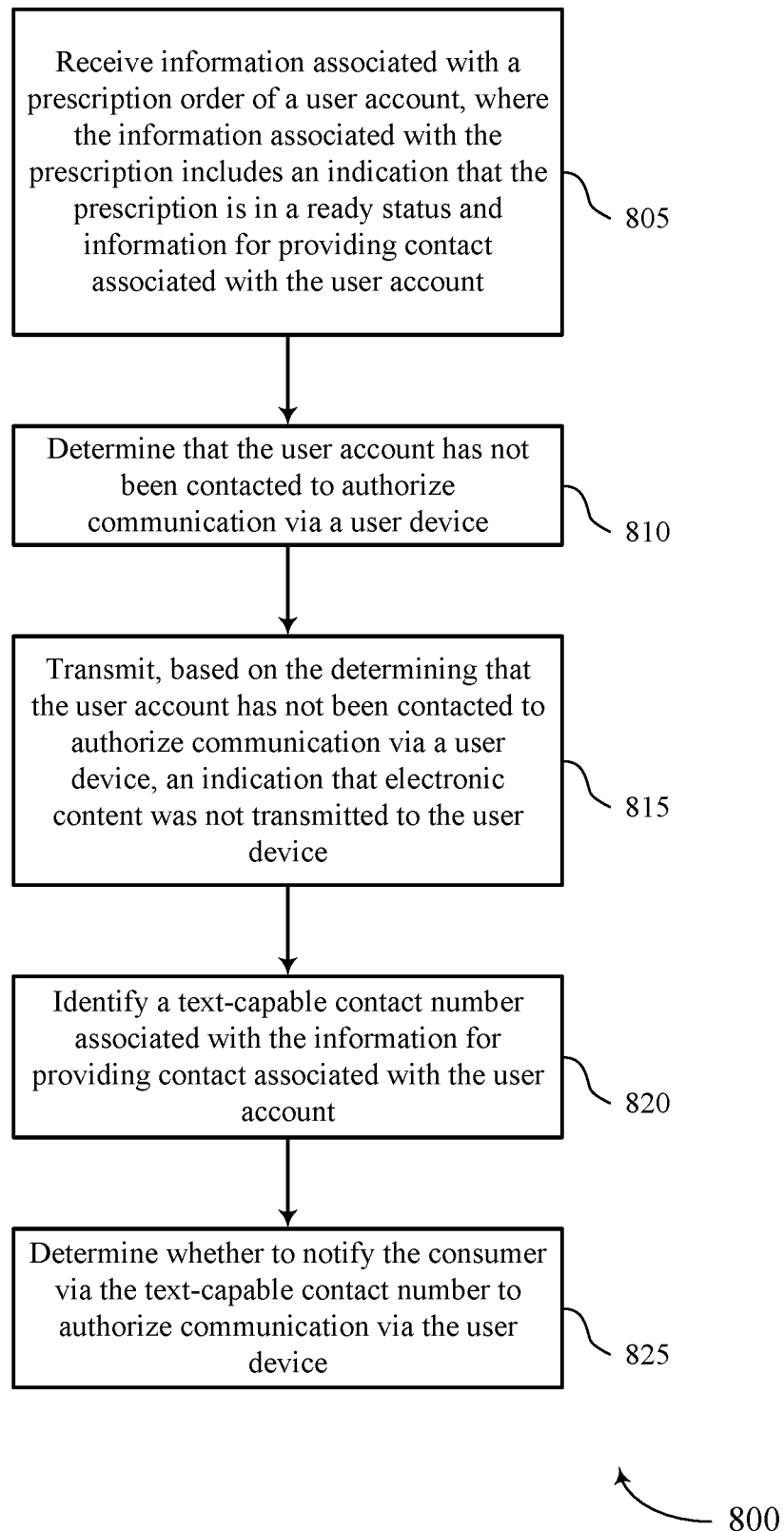

FIG. 8 shows a flowchart illustrating a method 800 that supports automated electronic medication documentation and sponsored content delivery system in accordance with aspects of the present disclosure. The operations of method 800 may be implemented by a server or its components as described herein. For example, the operations of method 800 may be performed by an electronic content delivery manager as described with reference to FIGS. 4 through 6. In some examples, a server may execute a set of instructions to control the functional elements of the server to perform the functions described below. Additionally or alternatively, a server may perform aspects of the functions described below using special-purpose hardware.

At 805, the server may receive information associated with the prescription order of a user account, where the information associated with the prescription includes an indication that the prescription is in a ready status and information for providing contact associated with the user account. The operations of 805 may be performed according to the methods described herein. In some examples, aspects of the operations of 805 may be performed by an apparatus or system as described with reference to FIGS. 4 through 6.

At 810, the server may determine that the user account has not been contacted to authorize communication via a user device. The operations of 810 may be performed according to the methods described herein. In some examples, aspects of the operations of 810 may be performed by an apparatus or system as described with reference to FIGS. 4 through 6.

At 815, the server may transmit, based on the determining that the user account has not been contacted to authorize communication via a user device, an indication that electronic content was not transmitted to the user device. The operations of 815 may be performed according to the methods described herein. In some examples, aspects of the operations of 815 may be performed by an apparatus or system as described with reference to FIGS. 4 through 6.

At 820, the server may identify a text-capable contact number associated with the information for providing contact associated with the user account. The operations of 820 may be performed according to the methods described herein. In some examples, aspects of the operations of 820 may be performed by an apparatus or system as described with reference to FIGS. 4 through 6.

At 825, the server may determine whether to notify a user of the user account via the text-capable contact number to authorize communication via the user device. The operations of 825 may be performed according to the methods described herein. In some examples, aspects of the operations of 825 may be performed by an apparatus or system as described with reference to FIGS. 4 through 6.

Figure 9:
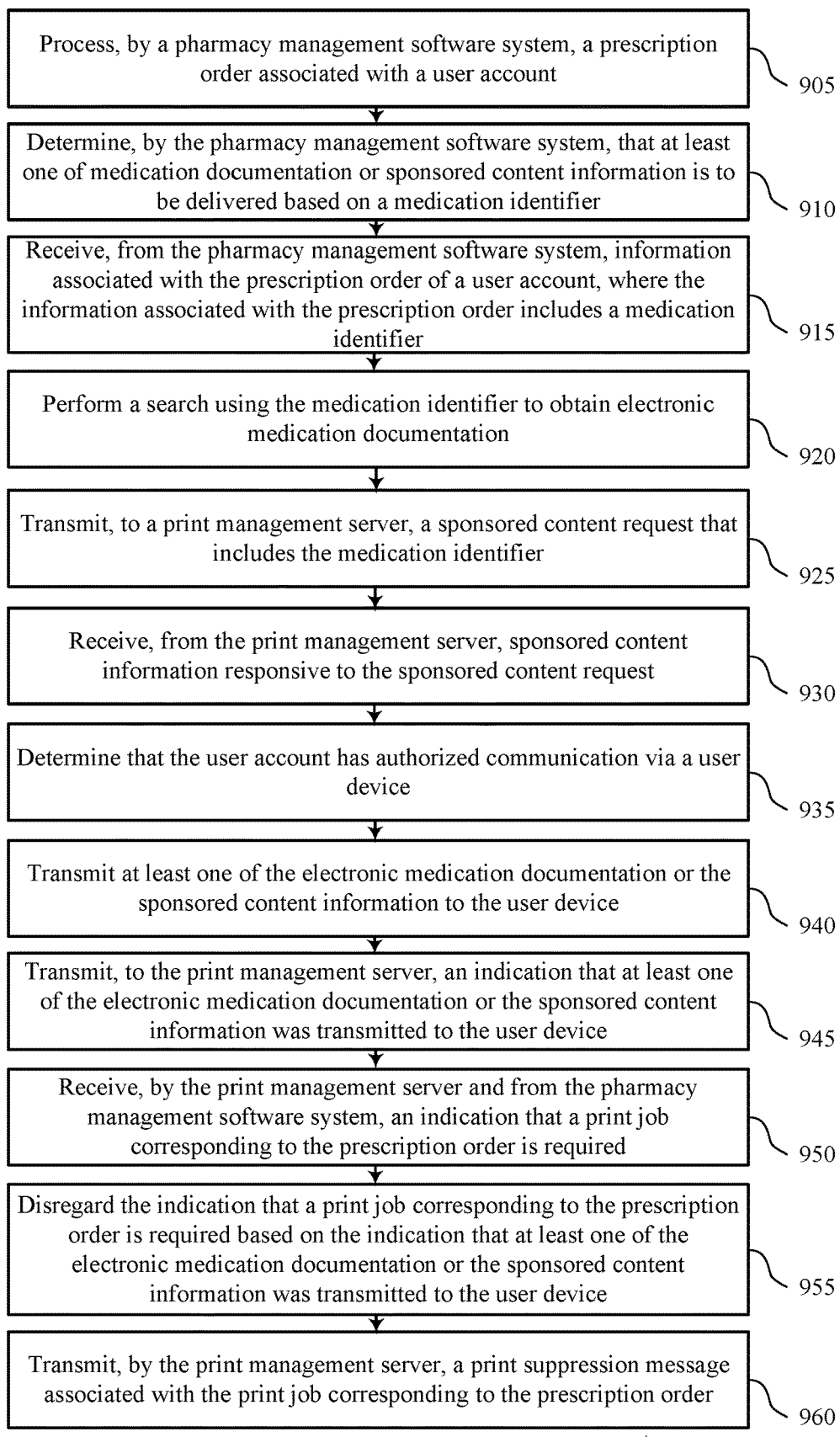

FIG. 9 shows a flowchart illustrating a method 900 that supports automated electronic medication documentation and sponsored content delivery system in accordance with aspects of the present disclosure. The operations of method 900 may be implemented by a server or its components as described herein. For example, the operations of method 900 may be performed by an electronic content delivery manager as described with reference to FIGS. 4 through 6. In some examples, a server may execute a set of instructions to control the functional elements of the server to perform the functions described below. Additionally or alternatively, a server may perform aspects of the functions described below using special-purpose hardware.

At 905, the server may process, by a pharmacy management software system, a prescription order associated with a user account. The operations of 905 may be performed according to the methods described herein. In some examples, aspects of the operations of 905 may be performed by an apparatus or system as described with reference to FIGS. 4 through 6.

At 910, the server may determine, by the pharmacy management software system, that at least one of medication documentation or sponsored content information is to be delivered based on a medication identifier. The operations of 910 may be performed according to the methods described herein. In some examples, aspects of the operations of 910 may be performed by an apparatus or system as described with reference to FIGS. 4 through 6.

At 915, the server may obtain, by the pharmacy management software system, information associated with the prescription order of a user account, where the information associated with the prescription order includes a medication identifier. The operations of 915 may be performed according to the methods described herein. In some examples, aspects of the operations of 915 may be performed by an apparatus or system as described with reference to FIGS. 4 through 6.

At 920, the server may perform a search using the medication identifier to obtain electronic medication documentation. The operations of 920 may be performed according to the methods described herein. In some examples, aspects of the operations of 920 may be performed by an apparatus or system as described with reference to FIGS. 4 through 6.

At 925, the server may transmit, to a print management server, a sponsored content request that includes the medication identifier. The operations of 925 may be performed according to the methods described herein. In some examples, aspects of the operations of 925 may be performed by an apparatus or system as described with reference to FIGS. 4 through 6.

At 930, the server may receive, from the print management server, sponsored content information responsive to the sponsored content request. The operations of 930 may be performed according to the methods described herein. In some examples, aspects of the operations of 930 may be performed by an apparatus or system as described with reference to FIGS. 4 through 6.

At 935, the server may determine that the user account has authorized communication via a user device. The operations of 935 may be performed according to the methods described herein. In some examples, aspects of the operations of 935 may be performed by an apparatus or system as described with reference to FIGS. 4 through 6.

At 940, the server may transmit at least one of the electronic medication documentation or the sponsored content information to the user device. The operations of 940 may be performed according to the methods described herein. In some examples, aspects of the operations of 940 may be performed by an apparatus or system as described with reference to FIGS. 4 through 6.

At 945, the server may transmit, to the print management server, an indication that at least one of the electronic medication documentation or the sponsored content information was transmitted to the user device. The operations of 945 may be performed according to the methods described herein. In some examples, aspects of the operations of 945 may be performed by an apparatus or system as described with reference to FIGS. 4 through 6.

At 950, the server may receive, by the print management server and from the pharmacy management software system, an indication that a print job corresponding to the prescription order is required. The operations of 950 may be performed according to the methods described herein. In some examples, aspects of the operations of 950 may be performed by an apparatus or system as described with reference to FIGS. 4 through 6.

At 955, the server may disregard the indication that a print job corresponding to the prescription order is required based on the indication that at least one of the electronic medication documentation or the sponsored content information was transmitted to the user device. The operations of 955 may be performed according to the methods described herein. In some examples, aspects of the operations of 955 may be performed by an apparatus or system as described with reference to FIGS. 4 through 6.

At 960, the server may transmit, by the print management server, a print suppression message associated with the print job corresponding to the prescription order. The operations of 960 may be performed according to the methods described herein. In some examples, aspects of the operations of 960 may be performed by an apparatus or system as described with reference to FIGS. 4 through 6.

Figure 10:
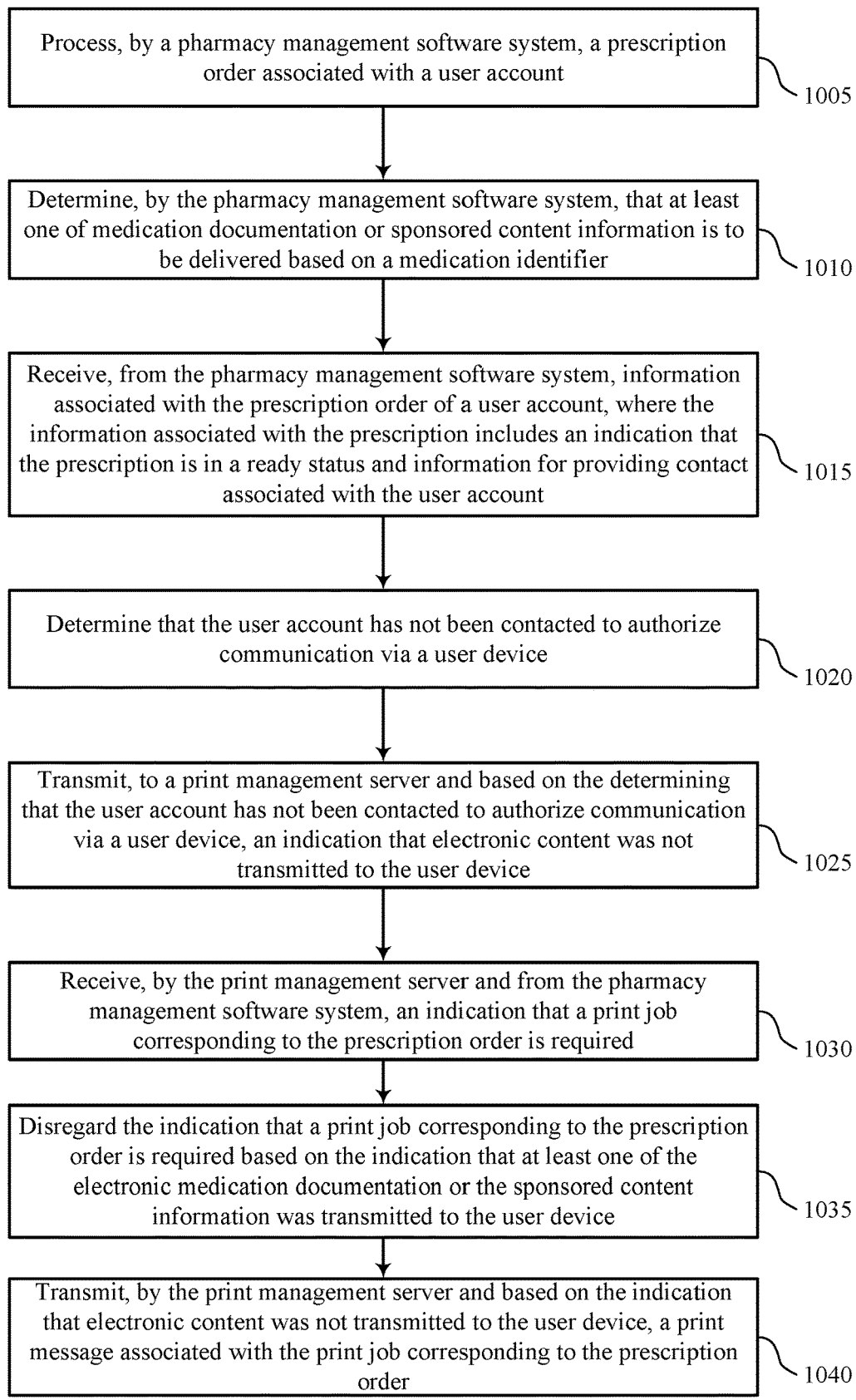

FIG. 10 shows a flowchart illustrating a method 1000 that supports automated electronic medication documentation and sponsored content delivery system in accordance with aspects of the present disclosure. The operations of method 1000 may be implemented by a server or its components as described herein. For example, the operations of method 1000 may be performed by an electronic content delivery manager as described with reference to FIGS. 4 through 6. In some examples, a server may execute a set of instructions to control the functional elements of the server to perform the functions described below. Additionally or alternatively, a server may perform aspects of the functions described below using special-purpose hardware.

At 1005, the server may process, by a pharmacy management software system, a prescription order associated with a user account. The operations of 1005 may be performed according to the methods described herein. In some examples, aspects of the operations of 1005 may be performed by an apparatus or system as described with reference to FIGS. 4 through 6.

At 1010, the server may determine, by the pharmacy management software system, that at least one of medication documentation or sponsored content information is to be delivered based on a medication identifier. The operations of 1010 may be performed according to the methods described herein. In some examples, aspects of the operations of 1010 may be performed by an apparatus or system as described with reference to FIGS. 4 through 6.

At 1015, the server may obtain, by the pharmacy management software system, information associated with the prescription order of a user account, where the information associated with the prescription includes an indication that the prescription is in a ready status and information for providing contact associated with the user account. The operations of 1015 may be performed according to the methods described herein. In some examples, aspects of the operations of 1015 may be performed by an apparatus or system as described with reference to FIGS. 4 through 6.

At 1020, the server may determine that the user account has not been contacted to authorize communication via a user device. The operations of 1020 may be performed according to the methods described herein. In some examples, aspects of the operations of 1020 may be performed by an apparatus or system as described with reference to FIGS. 4 through 6.

At 1025, the server may transmit, to a print management server and based on the determining that the user account has not been contacted to authorize communication via a user device, an indication that electronic content was not transmitted to the user device. The operations of 1025 may be performed according to the methods described herein. In some examples, aspects of the operations of 1025 may be performed by an apparatus or system as described with reference to FIGS. 4 through 6.

At 1030, the server may receive, by the print management server and from the pharmacy management software system, an indication that a print job corresponding to the prescription order is required. The operations of 1030 may be performed according to the methods described herein. In some examples, aspects of the operations of 1030 may be performed by an apparatus or system as described with reference to FIGS. 4 through 6.

At 1035, the server may disregard the indication that a print job corresponding to the prescription order is required based on the indication that at least one of the electronic medication documentation or the sponsored content information was transmitted to the user device. The operations of 1035 may be performed according to the methods described herein. In some examples, aspects of the operations of 1035 may be performed by an apparatus or system as described with reference to FIGS. 4 through 6.

At 1040, the server may transmit, by the print management server and based on the indication that electronic content was not transmitted to the user device, a print message associated with the print job corresponding to the prescription order. The operations of 1040 may be performed according to the methods described herein. In some examples, aspects of the operations of 1040 may be performed by an apparatus or system as described with reference to FIGS. 4 through 6.

Figure 11:
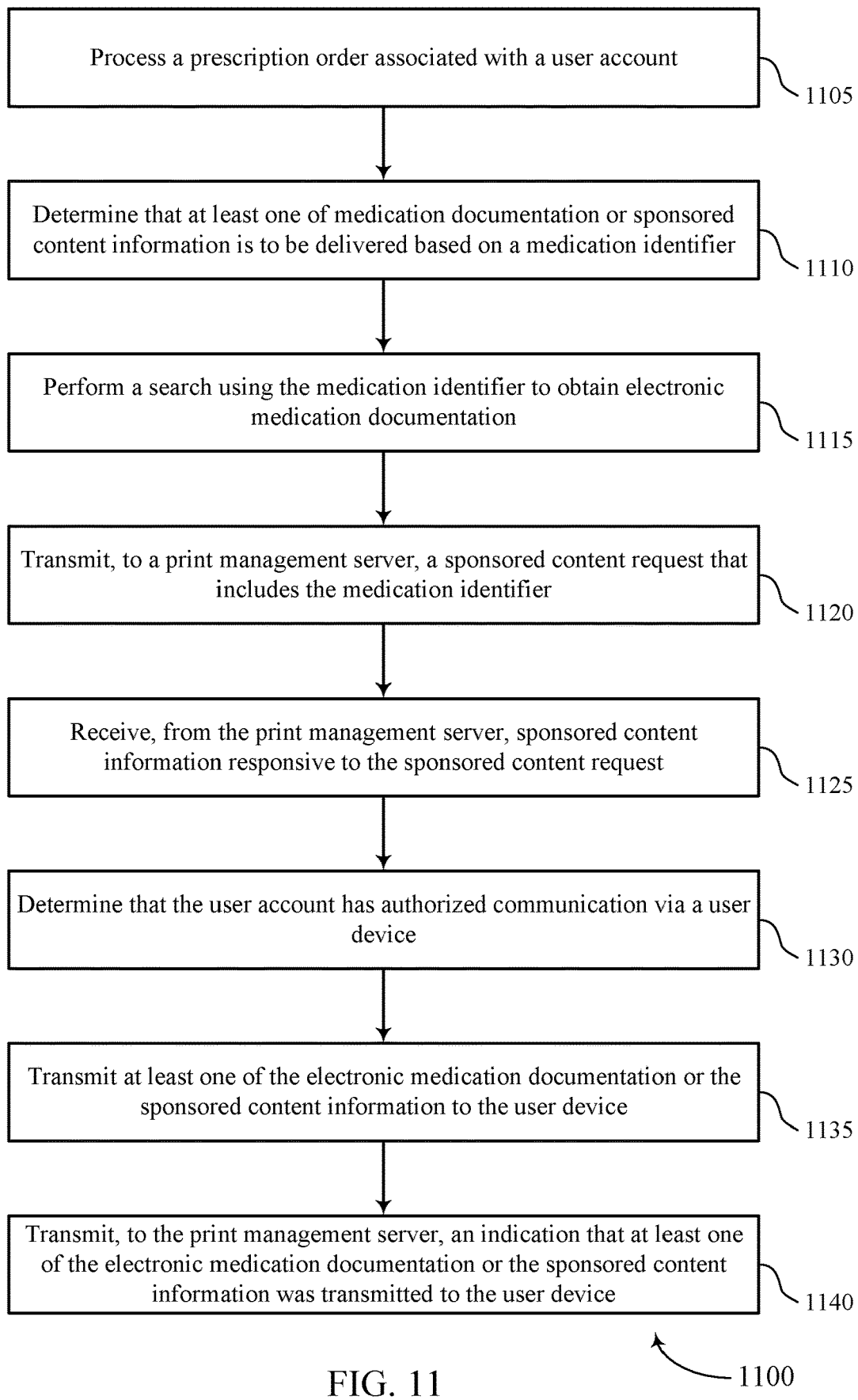

FIG. 11 shows a flowchart illustrating a method 1100 that supports automated electronic medication documentation and sponsored content delivery system in accordance with aspects of the present disclosure. The operations of method 1100 may be implemented by a server or its components as described herein. For example, the operations of method 1100 may be performed by an electronic content delivery manager as described with reference to FIGS. 4 through 6. In some examples, a server may execute a set of instructions to control the functional elements of the server to perform the functions described below. Additionally or alternatively, a server may perform aspects of the functions described below using special-purpose hardware.

At 1105, the server may process a prescription order associated with a user account. The operations of 1105 may be performed according to the methods described herein. In some examples, aspects of the operations of 1105 may be performed by an apparatus or system as described with reference to FIGS. 4 through 6.

At 1110, the server may determine that at least one of medication documentation or sponsored content information is to be delivered based on a medication identifier. The operations of 1110 may be performed according to the methods described herein. In some examples, aspects of the operations of 1110 may be performed by an apparatus or system as described with reference to FIGS. 4 through 6.

At 1115, the server may perform a search using the medication identifier to obtain electronic medication documentation. The operations of 1115 may be performed according to the methods described herein. In some examples, aspects of the operations of 1115 may be performed by an apparatus or system as described with reference to FIGS. 4 through 6.

At 1120, the server may transmit, to a print management server, a sponsored content request that includes the medication identifier. The operations of 1120 may be performed according to the methods described herein. In some examples, aspects of the operations of 1120 may be performed by an apparatus or system as described with reference to FIGS. 4 through 6.

At 1125, the server may receive, from the print management server, sponsored content information responsive to the sponsored content request. The operations of 1125 may be performed according to the methods described herein. In some examples, aspects of the operations of 1125 may be performed by an apparatus or system as described with reference to FIGS. 4 through 6.

At 1130, the server may determine that the user account has authorized communication via a user device. The operations of 1130 may be performed according to the methods described herein. In some examples, aspects of the operations of 1130 may be performed by an apparatus or system as described with reference to FIGS. 4 through 6.

At 1135, the server may transmit at least one of the electronic medication documentation or the sponsored content information to the user device. The operations of 1135 may be performed according to the methods described herein. In some examples, aspects of the operations of 1135 may be performed by an apparatus or system as described with reference to FIGS. 4 through 6.

At 1140, the server may transmit, to the print management server, an indication that at least one of the electronic medication documentation or the sponsored content information was transmitted to the user device. The operations of 1140 may be performed according to the methods described herein. In some examples, aspects of the operations of 1140 may be performed by an apparatus or system as described with reference to FIGS. 4 through 6.

Figure 12:
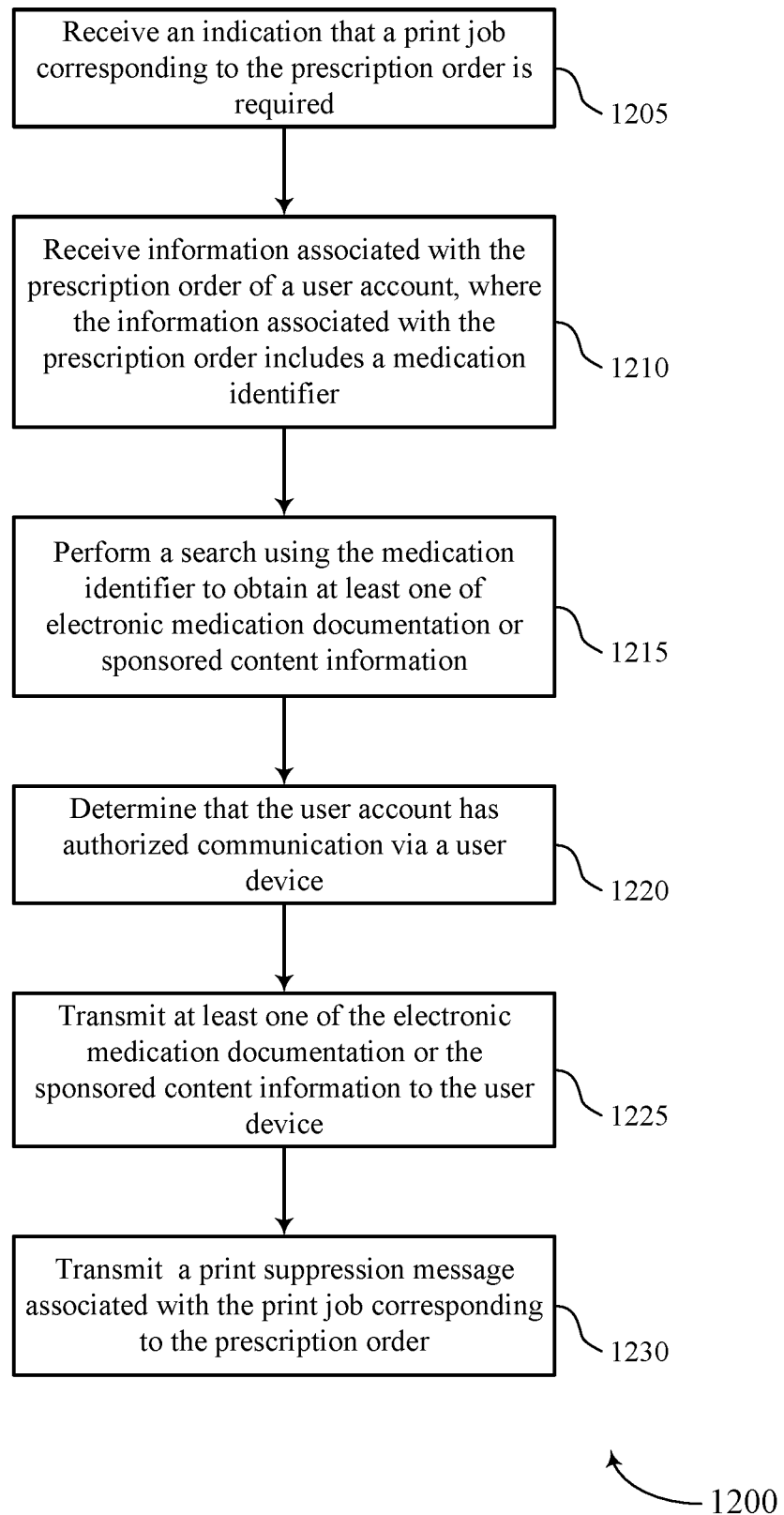

FIG. 12 shows a flowchart illustrating a method 1200 that supports automated electronic medication documentation and sponsored content delivery system in accordance with aspects of the present disclosure. The operations of method 1200 may be implemented by a server or its components as described herein. For example, the operations of method 1200 may be performed by an electronic content delivery manager as described with reference to FIGS. 4 through 6. In some examples, a server may execute a set of instructions to control the functional elements of the server to perform the functions described below. Additionally or alternatively, a server may perform aspects of the functions described below using special-purpose hardware.

At 1205, the server may receive an indication that a print job corresponding to the prescription order is required. The operations of 1205 may be performed according to the methods described herein. In some examples, aspects of the operations of 1205 may be performed by an apparatus or system as described with reference to FIGS. 4 through 6.

At 1210, the server may receive information associated with the prescription order of a user account, where the information associated with the prescription order includes a medication identifier. The operations of 1210 may be performed according to the methods described herein. In some examples, aspects of the operations of 1210 may be performed by an apparatus or system as described with reference to FIGS. 4 through 6.

At 1215, the server may perform a search using the medication identifier to obtain at least one of electronic medication documentation or sponsored content information. The operations of 1215 may be performed according to the methods described herein. In some examples, aspects of the operations of 1215 may be performed by an apparatus or system as described with reference to FIGS. 4 through 6.

At 1220, the server may determine that the user account has authorized communication via a user device. The operations of 1220 may be performed according to the methods described herein. In some examples, aspects of the operations of 1220 may be performed by an apparatus or system as described with reference to FIGS. 4 through 6.

At 1225, the server may transmit at least one of the electronic medication documentation or the sponsored content information to the user device. The operations of 1225 may be performed according to the methods described herein. In some examples, aspects of the operations of 1225 may be performed by an apparatus or system as described with reference to FIGS. 4 through 6.

At 1230, the server may transmit a print suppression message associated with the print job corresponding to the prescription order. The operations of 1230 may be performed according to the methods described herein. In some examples, aspects of the operations of 1230 may be performed by an apparatus or system as described with reference to FIGS. 4 through 6.

The following provides an overview of examples of the present disclosure:

Example Method 1: A method of electronic content delivery is described. The method may include receiving information associated with the prescription order of a user account, where the information associated with the prescription order includes a medication identifier, performing a search using the medication identifier to obtain electronic medication documentation, transmitting a sponsored content request that includes the medication identifier, receiving sponsored content information responsive to the sponsored content request, determining that the user account has authorized communication via a user device, transmitting at least one of the electronic medication documentation or the sponsored content information to the user device, and transmitting an indication that at least one of the electronic medication documentation or the sponsored content information was transmitted to the user device.

An apparatus for electronic content delivery is described. The apparatus may include a processor, memory coupled with the processor, and instructions stored in the memory. The instructions may be executable by the processor to cause the apparatus to receive information associated with the prescription order of a user account, where the information associated with the prescription order includes a medication identifier, perform a search using the medication identifier to obtain electronic medication documentation, transmit a sponsored content request that includes the medication identifier, receive sponsored content information responsive to the sponsored content request, determine that the user account has authorized communication via a user device, transmit at least one of the electronic medication documentation or the sponsored content information to the user device, and transmit an indication that at least one of the electronic medication documentation or the sponsored content information was transmitted to the user device.

Another apparatus for electronic content delivery is described. The apparatus may include means for receiving information associated with the prescription order of a user account, where the information associated with the prescription order includes a medication identifier, performing a search using the medication identifier to obtain electronic medication documentation, transmitting a sponsored content request that includes the medication identifier, receiving sponsored content information responsive to the sponsored content request, determining that the user account has authorized communication via a user device, transmitting at least one of the electronic medication documentation or the sponsored content information to the user device, and transmitting an indication that at least one of the electronic medication documentation or the sponsored content information was transmitted to the user device.

A non-transitory computer-readable medium storing code for electronic content delivery is described. The code may include instructions executable by a processor to receive information associated with the prescription order of a user account, where the information associated with the prescription order includes a medication identifier, perform a search using the medication identifier to obtain electronic medication documentation, transmit a sponsored content request that includes the medication identifier, receive sponsored content information responsive to the sponsored content request, determine that the user account has authorized communication via a user device, transmit at least one of the electronic medication documentation or the sponsored content information to the user device, and transmit an indication that at least one of the electronic medication documentation or the sponsored content information was transmitted to the user device.

Example Method 2: A method of electronic content delivery is described. The method may include receiving information associated with a prescription order of a user account, where the information associated with the prescription includes an indication that the prescription is in a ready status and information for providing contact associated with the user account, determining that the user account has not been contacted to authorize communication via a user device, and transmitting, based on the determining that the user account has not been contacted to authorize communication via a user device, an indication that electronic content was not transmitted to the user device.

An apparatus for electronic content delivery is described. The apparatus may include a processor, memory coupled with the processor, and instructions stored in the memory. The instructions may be executable by the processor to cause the apparatus to receive information associated with a prescription order of a user account, where the information associated with the prescription includes an indication that the prescription is in a ready status and information for providing contact associated with the user account, determine that the user account has not been contacted to authorize communication via a user device, and transmit, based on the determining that the user account has not been contacted to authorize communication via a user device, an indication that electronic content was not transmitted to the user device.

Another apparatus for electronic content delivery is described. The apparatus may include means for receiving information associated with a prescription order of a user account, where the information associated with the prescription includes an indication that the prescription is in a ready status and information for providing contact associated with the user account, determining that the user account has not been contacted to authorize communication via a user device, and transmitting, based on the determining that the user account has not been contacted to authorize communication via a user device, an indication that electronic content was not transmitted to the user device.

A non-transitory computer-readable medium storing code for electronic content delivery is described. The code may include instructions executable by a processor to receive information associated with a prescription order of a user account, where the information associated with the prescription includes an indication that the prescription is in a ready status and information for providing contact associated with the user account, determine that the user account has not been contacted to authorize communication via a user device, and transmit, based on the determining that the user account has not been contacted to authorize communication via a user device, an indication that electronic content was not transmitted to the user device.

Some examples of the method, apparatuses, and non-transitory computer-readable medium described herein may further include operations, features, means, or instructions for identifying a text-capable contact number associated with the information for providing contact associated with the user account, and determining whether to notify a user of the user account via the text-capable contact number to authorize communication via the user device.

Example Method 3: A method of electronic content delivery is described. The method may include processing, by a pharmacy management software system, a prescription order associated with a user account, determining, by the pharmacy management software system, that at least one of medication documentation or sponsored content information is to be delivered based on a medication identifier, obtaining, by the pharmacy management software system, information associated with the prescription order of a user account, where the information associated with the prescription order includes a medication identifier, performing a search using the medication identifier to obtain electronic medication documentation, transmitting, to a print management server, a sponsored content request that includes the medication identifier, receiving, from the print management server, sponsored content information responsive to the sponsored content request, determining that the user account has authorized communication via a user device, transmitting at least one of the electronic medication documentation or the sponsored content information to the user device, transmitting, to the print management server, an indication that at least one of the electronic medication documentation or the sponsored content information was transmitted to the user device, receiving, by the print management server and from the pharmacy management software system, an indication that a print job corresponding to the prescription order is required, disregarding the indication that a print job corresponding to the prescription order is required based on the indication that at least one of the electronic medication documentation or the sponsored content information was transmitted to the user device, and transmitting, by the print management server, a print suppression message associated with the print job corresponding to the prescription order.

An apparatus for electronic content delivery is described. The apparatus may include a processor, memory coupled with the processor, and instructions stored in the memory. The instructions may be executable by the processor to cause the apparatus to process, by a pharmacy management software system, a prescription order associated with a user account, determine, by the pharmacy management software system, that at least one of medication documentation or sponsored content information is to be delivered based on a medication identifier, obtain, by the pharmacy management software system, information associated with the prescription order of a user account, where the information associated with the prescription order includes a medication identifier, perform a search using the medication identifier to obtain electronic medication documentation, transmit, to a print management server, a sponsored content request that includes the medication identifier, receive, from the print management server, sponsored content information responsive to the sponsored content request, determine that the user account has authorized communication via a user device, transmit at least one of the electronic medication documentation or the sponsored content information to the user device, transmit, to the print management server, an indication that at least one of the electronic medication documentation or the sponsored content information was transmitted to the user device, receive, by the print management server and from the pharmacy management software system, an indication that a print job corresponding to the prescription order is required, disregard the indication that a print job corresponding to the prescription order is required based on the indication that at least one of the electronic medication documentation or the sponsored content information was transmitted to the user device, and transmit, by the print management server, a print suppression message associated with the print job corresponding to the prescription order.

Another apparatus for electronic content delivery is described. The apparatus may include means for processing, by a pharmacy management software system, a prescription order associated with a user account, determining, by the pharmacy management software system, that at least one of medication documentation or sponsored content information is to be delivered based on a medication identifier, obtaining, by the pharmacy management software system, information associated with the prescription order of a user account, where the information associated with the prescription order includes a medication identifier, performing a search using the medication identifier to obtain electronic medication documentation, transmitting, to a print management server, a sponsored content request that includes the medication identifier, receiving, from the print management server, sponsored content information responsive to the sponsored content request, determining that the user account has authorized communication via a user device, transmitting at least one of the electronic medication documentation or the sponsored content information to the user device, transmitting, to the print management server, an indication that at least one of the electronic medication documentation or the sponsored content information was transmitted to the user device, receiving, by the print management server and from the pharmacy management software system, an indication that a print job corresponding to the prescription order is required, disregarding the indication that a print job corresponding to the prescription order is required based on the indication that at least one of the electronic medication documentation or the sponsored content information was transmitted to the user device, and transmitting, by the print management server, a print suppression message associated with the print job corresponding to the prescription order.

A non-transitory computer-readable medium storing code for electronic content delivery is described. The code may include instructions executable by a processor to process, by a pharmacy management software system, a prescription order associated with a user account, determine, by the pharmacy management software system, that at least one of medication documentation or sponsored content information is to be delivered based on a medication identifier, obtain, by the pharmacy management software system, information associated with the prescription order of a user account, where the information associated with the prescription order includes a medication identifier, perform a search using the medication identifier to obtain electronic medication documentation, transmit, to a print management server, a sponsored content request that includes the medication identifier, receive, from the print management server, sponsored content information responsive to the sponsored content request, determine that the user account has authorized communication via a user device, transmit at least one of the electronic medication documentation or the sponsored content information to the user device, transmit, to the print management server, an indication that at least one of the electronic medication documentation or the sponsored content information was transmitted to the user device, receive, by the print management server and from the pharmacy management software system, an indication that a print job corresponding to the prescription order is required, disregard the indication that a print job corresponding to the prescription order is required based on the indication that at least one of the electronic medication documentation or the sponsored content information was transmitted to the user device, and transmit, by the print management server, a print suppression message associated with the print job corresponding to the prescription order.

Example Method 4: A method of electronic content delivery is described. The method may include processing, by a pharmacy management software system, a prescription order associated with a user account, determining, by the pharmacy management software system, that at least one of medication documentation or sponsored content information is to be delivered based on a medication identifier, obtaining, by the pharmacy management software system, information associated with the prescription order of a user account, where the information associated with the prescription includes an indication that the prescription is in a ready status and information for providing contact associated with the user account, determining that the user account has not been contacted to authorize communication via a user device, transmitting, to a print management server and based on the determining that the user account has not been contacted to authorize communication via a user device, an indication that electronic content was not transmitted to the user device, receiving, by the print management server and from the pharmacy management software system, an indication that a print job corresponding to the prescription order is required, disregarding the indication that a print job corresponding to the prescription order is required based on the indication that at least one of the electronic medication documentation or the sponsored content information was transmitted to the user device, and transmitting, by the print management server and based on the indication that electronic content was not transmitted to the user device, a print message associated with the print job corresponding to the prescription order.

An apparatus for electronic content delivery is described. The apparatus may include a processor, memory coupled with the processor, and instructions stored in the memory. The instructions may be executable by the processor to cause the apparatus to process, by a pharmacy management software system, a prescription order associated with a user account, determine, by the pharmacy management software system, that at least one of medication documentation or sponsored content information is to be delivered based on a medication identifier, obtain, by the pharmacy management software system, information associated with the prescription order of a user account, where the information associated with the prescription includes an indication that the prescription is in a ready status and information for providing contact associated with the user account, determine that the user account has not been contacted to authorize communication via a user device, transmit, to a print management server and based on the determining that the user account has not been contacted to authorize communication via a user device, an indication that electronic content was not transmitted to the user device, receive, by the print management server and from the pharmacy management software system, an indication that a print job corresponding to the prescription order is required, disregard the indication that a print job corresponding to the prescription order is required based on the indication that at least one of the electronic medication documentation or the sponsored content information was transmitted to the user device, and transmit, by the print management server and based on the indication that electronic content was not transmitted to the user device, a print message associated with the print job corresponding to the prescription order.

Another apparatus for electronic content delivery is described. The apparatus may include means for processing, by a pharmacy management software system, a prescription order associated with a user account, determining, by the pharmacy management software system, that at least one of medication documentation or sponsored content information is to be delivered based on a medication identifier, obtaining, by the pharmacy management software system, information associated with the prescription order of a user account, where the information associated with the prescription includes an indication that the prescription is in a ready status and information for providing contact associated with the user account, determining that the user account has not been contacted to authorize communication via a user device, transmitting, to a print management server and based on the determining that the user account has not been contacted to authorize communication via a user device, an indication that electronic content was not transmitted to the user device, receiving, by the print management server and from the pharmacy management software system, an indication that a print job corresponding to the prescription order is required, disregarding the indication that a print job corresponding to the prescription order is required based on the indication that at least one of the electronic medication documentation or the sponsored content information was transmitted to the user device, and transmitting, by the print management server and based on the indication that electronic content was not transmitted to the user device, a print message associated with the print job corresponding to the prescription order.

A non-transitory computer-readable medium storing code for electronic content delivery is described. The code may include instructions executable by a processor to process, by a pharmacy management software system, a prescription order associated with a user account, determine, by the pharmacy management software system, that at least one of medication documentation or sponsored content information is to be delivered based on a medication identifier, obtain, by the pharmacy management software system, information associated with the prescription order of a user account, where the information associated with the prescription includes an indication that the prescription is in a ready status and information for providing contact associated with the user account, determine that the user account has not been contacted to authorize communication via a user device, transmit, to a print management server and based on the determining that the user account has not been contacted to authorize communication via a user device, an indication that electronic content was not transmitted to the user device, receive, by the print management server and from the pharmacy management software system, an indication that a print job corresponding to the prescription order is required, disregard the indication that a print job corresponding to the prescription order is required based on the indication that at least one of the electronic medication documentation or the sponsored content information was transmitted to the user device, and transmit, by the print management server and based on the indication that electronic content was not transmitted to the user device, a print message associated with the print job corresponding to the prescription order.

Example Method 5: A method of electronic content delivery is described. The method may include processing a prescription order associated with a user account, determining that at least one of medication documentation or sponsored content information is to be delivered based on a medication identifier, performing a search using the medication identifier to obtain electronic medication documentation, transmitting, to a print management server, a sponsored content request that includes the medication identifier, receiving, from the print management server, sponsored content information responsive to the sponsored content request, determining that the user account has authorized communication via a user device, transmitting at least one of the electronic medication documentation or the sponsored content information to the user device, and transmitting, to the print management server, an indication that at least one of the electronic medication documentation or the sponsored content information was transmitted to the user device.

An apparatus for electronic content delivery is described. The apparatus may include a processor, memory coupled with the processor, and instructions stored in the memory. The instructions may be executable by the processor to cause the apparatus to process a prescription order associated with a user account, determine that at least one of medication documentation or sponsored content information is to be delivered based on a medication identifier, perform a search using the medication identifier to obtain electronic medication documentation, transmit, to a print management server, a sponsored content request that includes the medication identifier, receive, from the print management server, sponsored content information responsive to the sponsored content request, determine that the user account has authorized communication via a user device, transmit at least one of the electronic medication documentation or the sponsored content information to the user device, and transmit, to the print management server, an indication that at least one of the electronic medication documentation or the sponsored content information was transmitted to the user device.

Another apparatus for electronic content delivery is described. The apparatus may include means for processing a prescription order associated with a user account, determining that at least one of medication documentation or sponsored content information is to be delivered based on a medication identifier, performing a search using the medication identifier to obtain electronic medication documentation, transmitting, to a print management server, a sponsored content request that includes the medication identifier, receiving, from the print management server, sponsored content information responsive to the sponsored content request, determining that the user account has authorized communication via a user device, transmitting at least one of the electronic medication documentation or the sponsored content information to the user device, and transmitting, to the print management server, an indication that at least one of the electronic medication documentation or the sponsored content information was transmitted to the user device.

A non-transitory computer-readable medium storing code for electronic content delivery is described. The code may include instructions executable by a processor to process a prescription order associated with a user account, determine that at least one of medication documentation or sponsored content information is to be delivered based on a medication identifier, perform a search using the medication identifier to obtain electronic medication documentation, transmit, to a print management server, a sponsored content request that includes the medication identifier, receive, from the print management server, sponsored content information responsive to the sponsored content request, determine that the user account has authorized communication via a user device, transmit at least one of the electronic medication documentation or the sponsored content information to the user device, and transmit, to the print management server, an indication that at least one of the electronic medication documentation or the sponsored content information was transmitted to the user device.

Example Method 6: A method of electronic content delivery is described. The method may include receiving an indication that a print job corresponding to the prescription order is required, receiving information associated with the prescription order of a user account, where the information associated with the prescription order includes a medication identifier, performing a search using the medication identifier to obtain at least one of electronic medication documentation or sponsored content information, determining that the user account has authorized communication via a user device, transmitting at least one of the electronic medication documentation or the sponsored content information to the user device, and transmitting a print suppression message associated with the print job corresponding to the prescription order.

An apparatus for electronic content delivery is described. The apparatus may include a processor, memory coupled with the processor, and instructions stored in the memory. The instructions may be executable by the processor to cause the apparatus to receive an indication that a print job corresponding to the prescription order is required, receive information associated with the prescription order of a user account, where the information associated with the prescription order includes a medication identifier, perform a search using the medication identifier to obtain at least one of electronic medication documentation or sponsored content information, determine that the user account has authorized communication via a user device, transmit at least one of the electronic medication documentation or the sponsored content information to the user device, and transmit a print suppression message associated with the print job corresponding to the prescription order.

Another apparatus for electronic content delivery is described. The apparatus may include means for receiving an indication that a print job corresponding to the prescription order is required, receiving information associated with the prescription order of a user account, where the information associated with the prescription order includes a medication identifier, performing a search using the medication identifier to obtain at least one of electronic medication documentation or sponsored content information, determining that the user account has authorized communication via a user device, transmitting at least one of the electronic medication documentation or the sponsored content information to the user device, and transmitting a print suppression message associated with the print job corresponding to the prescription order.

A non-transitory computer-readable medium storing code for electronic content delivery is described. The code may include instructions executable by a processor to receive an indication that a print job corresponding to the prescription order is required, receive information associated with the prescription order of a user account, where the information associated with the prescription order includes a medication identifier, perform a search using the medication identifier to obtain at least one of electronic medication documentation or sponsored content information, determine that the user account has authorized communication via a user device, transmit at least one of the electronic medication documentation or the sponsored content information to the user device, and transmit a print suppression message associated with the print job corresponding to the prescription order.

It should be noted that the example methods described above describe possible implementations, and that the operations and the steps may be rearranged or otherwise modified and that other implementations are possible. Furthermore, aspects from two or more of the example methods may be combined.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable read only memory (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A method for electronic content delivery by a computing device interfacing with a pharmacy management software server, comprising:
   receiving, by the computing device and from the pharmacy management software server, information associated with a prescription order of a user account, wherein the information associated with the prescription order comprises a medication identifier;
   determining, based at least in part on the medication identifier, that sponsored content is available for the prescription order;
   transmitting, by the computing device and to a content server different from the pharmacy management software server, a sponsored content request that includes at least a portion of the medication identifier;
   receiving, by the computing device and from the content server, sponsored content information responsive to the sponsored content request, wherein the sponsored content information comprises electronic content information different from electronic medication documentation corresponding to a medication of the prescription order, the electronic medication documentation including patient instructions for taking the medication;
   determining, by the computing device, that the user account has authorized communication via a user device of a user;
   transmitting, by the computing device, the sponsored content information to the user device of the user; and
   transmitting, by the computing device, an indication that the sponsored content information was transmitted to the user device of the user.

2. The method of claim 1, wherein the medication identifier comprises at least one of a drug name, a national drug code or a generic product identifier.

3. The method of claim 1, wherein the information associated with the prescription order comprises an indication that the prescription order is in a ready status.

4. The method of claim 1, wherein the information associated with the prescription order comprises information for providing contact associated with the user account.

5. The method of claim 4, wherein the information for providing contact associated with the user account comprises at least one of a primary contact number or a patient identifier.

6. The method of claim 1, wherein the electronic medication documentation comprises a medication-related document.

7. The method of claim 1, wherein the electronic content information comprises a uniform resource locator.

8. The method of claim 1, wherein the user device is a device associated with a text-capable number.

9. The method of claim 1, wherein the user device is a mobile device.

10. The method of claim 1, wherein the electronic content information is associated with a medication different from a medication associated with the prescription order.

11. The method of claim 1, wherein the electronic content information is associated with a product for administering a medication associated with the prescription order.

12. The method of claim 11, wherein the electronic content information comprises a uniform resource locator linking a video demonstration of the product for administering the medication associated with the prescription order.

13. The method of claim 1, wherein the electronic content information is associated with a procedure temporally associated with a fulfilment date of the prescription order and unrelated to the prescription order.

14. The method of claim 1, wherein:
   the determining that sponsored content is available for the prescription order is based at least in part on a first section of the medication identifier that identifies a drug product irrespective of a manufacturer; and
   the sponsored content request that is transmitted to the content server different from the pharmacy management software server includes the first section of the medication identifier that identifies the drug product irrespective of the manufacturer.

15. A method for electronic content delivery by a computing device interfacing with a pharmacy management software server, comprising:
   receiving, by the computing device and from the pharmacy management software server, information associated with a prescription order of a user account, wherein the information associated with the prescription order comprises an indication that the prescription order is in a ready status, a medication identifier and information for providing contact associated with the user account;

determining, by the computing device, that the user account has not been contacted to authorize communication via a user device of a user;

transmitting, by the computing device and based at least in part on the determining that the user account has not been contacted to authorize communication via the user device of the user, an indication that electronic medication documentation content was not transmitted to the user device;

identifying, by the computing device, a text-capable contact number associated with the information for providing contact associated with the user account;

notifying, by the computing device, a user of the user account via the text-capable contact number to authorize communication via the user device of the user based at least in part on the determining that the user account has not been contacted to authorize communication via the user device of the user; and transmitting, by the computing device and in response to an authorization for communication via the user device of the user, the electronic medication documentation.

16. The method of claim 15, wherein the information for providing contact associated with the user account comprises at least one of a primary contact number or a patient identifier.

17. The method of claim 15, wherein determining that the user account has not been contacted to authorize communication via the user device of the user comprises determining that the receiving information associated with the prescription order of the user account is a first instance for receiving information for providing contact associated with the user account.

18. The method of claim 15, further comprising:

identifying a contact number associated with the information for providing contact associated with the user account;

placing an outbound call to the contact number based at least in part on receiving the receiving information associated with the prescription order of the user account; and providing a message and a prompt to indicate whether to provide printed medication documentation at a location or the electronic medication documentation via the user device of the user.

19. A method for electronic content delivery by a computing device interfacing with a pharmacy management software server, comprising:

receiving, by the computing device and from the pharmacy management software server, an indication that a print job corresponding to a prescription order is required;

receiving, by the computing device, information associated with the prescription order of a user account, wherein the information associated with the prescription order comprises a medication identifier;

performing, by the computing device, a search using the medication identifier to obtain of electronic medication documentation or sponsored content information, wherein the electronic medication documentation corresponds to a medication of the prescription order including patient instructions for taking the medication;

determining, by the computing device, that the user account has authorized communication via a user device of a user;

transmitting, by the computing device, the electronic medication documentation to the user device of the user; and transmitting, by the computing device and to a print management server different from the pharmacy management software server, a print suppression message associated with the print job corresponding to the prescription order, wherein transmitting the print suppression message is based at least in part on transmitting the electronic medication documentation to the user device of the user.

\* \* \* \* \*